US012629211B2

(12) United States Patent
Kaethner et al.

(10) Patent No.: US 12,629,211 B2
(45) Date of Patent: May 19, 2026

(54) APPARATUS FOR POSITIONING A MEDICAL OBJECT AND METHOD FOR PROVIDING A CORRECTION SPECIFICATION

(71) Applicant: Siemens Healthcare GmbH, Erlangen (DE)

(72) Inventors: Christian Kaethner, Forchheim (DE); Tobias Lenich, Nuremberg (DE); Andreas Meyer, Bubenreuth (DE); Marcus Pfister, Bubenreuth (DE); Michael Wiets, Langensendelbach (DE)

(73) Assignee: Siemens Healthineers AG, Forchheim (DE)

( * ) Notice: Subject to any disclaimer, the term of this patent is extended or adjusted under 35 U.S.C. 154(b) by 253 days.

(21) Appl. No.: 17/484,113

(22) Filed: Sep. 24, 2021

(65) Prior Publication Data

US 2022/0087751 A1     Mar. 24, 2022

(30) Foreign Application Priority Data

Sep. 24, 2020    (DE) ..................... 10 2020 212 000.5

(51) Int. Cl.
*A61B 34/20*        (2016.01)
*A61B 34/32*        (2016.01)
(Continued)

(52) U.S. Cl.
CPC .............. *A61B 34/20* (2016.02); *A61B 34/32* (2016.02); *A61B 34/35* (2016.02); *A61B 2034/301* (2016.02)

(58) Field of Classification Search
CPC .... A61B 34/20; A61B 34/32; A61B 2034/301
See application file for complete search history.

(56) References Cited

U.S. PATENT DOCUMENTS 10,729,502 B1     8/2020  Wolf
2008/0119727 A1*  5/2008  Barbagli ................ A61B 90/36
                                                          600/437
(Continued)

FOREIGN PATENT DOCUMENTS

CN          101809618 A       8/2010
CN          108882837 A       11/2018
(Continued)

OTHER PUBLICATIONS

Cepolina et al., An introductory review of robotically assisted surgical systems, (2022), University of Genova. (Year: 2022).*

(Continued)

*Primary Examiner* — Brooke Lyn Klein
(74) *Attorney, Agent, or Firm* — Lempia Summerfield Katz LLC

(57) ABSTRACT

An apparatus for positioning a medical object includes a moving apparatus for robotically moving the medical object. The medical object includes a predefined section. The predefined section is at least partially arranged in an examination object. The apparatus is configured to receive a control specification. The moving apparatus is configured to position the predefined section based on the control specification. The apparatus is further configured to receive positioning information on the predefined section and determine a degree of deviation. The degree of deviation describes a deviation between the control specification and the positioning information. The apparatus is configured to determine a correction specification for minimizing the deviation based on the degree of deviation. The moving apparatus is further configured to reposition the predefined section based on the correction specification.

10 Claims, 10 Drawing Sheets

(51) Int. Cl.
    *A61B 34/35*        (2016.01)
    *A61B 34/30*        (2016.01)

(56)           References Cited

U.S. PATENT DOCUMENTS

| | | | |
|---|---|---|---|
| 2009/0149867 A1* | 6/2009 | Glozman | A61B 34/70 |
| | | | 600/407 |
| 2010/0168918 A1* | 7/2010 | Zhao | A61B 34/76 |
| | | | 702/41 |
| 2010/0226537 A1 | 9/2010 | Villain | |
| 2016/0228032 A1 | 8/2016 | Walker | |
| 2016/0302869 A1 | 10/2016 | Chopra | |
| 2016/0374541 A1 | 12/2016 | Agrawal et al. | |
| 2017/0151027 A1* | 6/2017 | Walker | A61B 34/30 |
| 2018/0092517 A1 | 4/2018 | Graetzel | |
| 2020/0129740 A1 | 4/2020 | Kottenstette et al. | |
| 2020/0202557 A1 | 6/2020 | Schmidt | |
| 2020/0214767 A1 | 7/2020 | Lonkadi | |

| | | | |
|---|---|---|---|
| 2020/0246088 A1 | 8/2020 | Mewes et al. | |
| 2021/0259780 A1* | 8/2021 | van der Zaag | A61B 34/20 |
| 2022/0211452 A1* | 7/2022 | Clark | B25J 13/065 |

FOREIGN PATENT DOCUMENTS

| | | |
|---|---|---|
| CN | 108882966 A | 11/2018 |
| CN | 111407403 A | 7/2020 |
| DE | 102019215001 A1 | 4/2021 |
| WO | 2020061240 A1 | 3/2020 |
| WO | 2020181006 A1 | 9/2020 |

OTHER PUBLICATIONS

Corindus Vascular Robotics; https://www.corindus.com/corpath-grx/how-it-works. Retrieved Sep. 20, 2021.

German Office Action for German Application No. 10 2020 212 000.5 dated Jun. 11, 2021.

* cited by examiner

APPARATUS FOR POSITIONING A MEDICAL OBJECT AND METHOD FOR PROVIDING A CORRECTION SPECIFICATION

This application claims the benefit of German Patent Application Number DE 10 2020 212 000.5, filed on Sep. 24, 2020, which is hereby incorporated by reference in its entirety.

BACKGROUND

The present embodiments relate to an apparatus for positioning a medical object, a system, a method for providing a correction specification, a method for providing a trained function, and a computer program product.

Interventional medical procedures in or via a vascular system of an examination object frequently require the (e.g., percutaneous) introduction of a, for example, elongated medical object into the vascular system. Further, successful diagnosis and/or treatment often requires at least part of the medical object to be guided toward a target region to be treated in the vascular system.

Movement of the medical object (e.g., translation and/or rotation) may result in meandering and/or spiraling of the medical object in the vascular system. This may cause a delayed reaction of a distal section of the medical object to a movement applied to a distal section (e.g., by an operator). Further, this may result in a difference in length and/or difference in angle between a prespecified target positioning and the actual positioning of the distal section. To compensate this difference in length and/or difference in angle, the medical object is often moved by the medical operator (e.g., manually) under regular X-ray fluoroscopy control. Herein, one drawback is the high X-ray exposure of the medical operator and the examination object. Further, without precise knowledge of the spatial course of the medical object in the vascular system (e.g., a manifestation of meandering and/or spiraling), positioning of the distal section is frequently subject to errors.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved positioning of a medical object is provided.

In a first aspect, an apparatus for positioning a medical object is provided. Herein, the apparatus includes a moving apparatus for robotically moving the medical object. Further, the medical object includes a predefined section. The predefined section is at least partially arranged in an examination object. Further, the apparatus is embodied to receive a control specification. The moving apparatus is further embodied to position the predefined section based on the control specification. The apparatus is further embodied to receive positioning information on the predefined section. Further, the apparatus is embodied to determine a degree of deviation. Herein, the degree of deviation describes a deviation between the control specification and the positioning information. Further, the apparatus is embodied to determine a correction specification for minimizing the deviation based on the degree of deviation. The moving apparatus is further embodied to reposition the predefined section based on the correction specification.

Herein, the medical object may, for example, be embodied as a surgical instrument and/or diagnostic instrument. For example, the medical object may be elongated and/or flexible. The medical object may, for example, be embodied as a catheter and/or endoscope and/or guide wire. The predefined section of the medical object may describe a spatial (e.g., distal) section of the medical object (e.g., an end and/or tip of the medical object).

The apparatus may further include a providing unit embodied to control the apparatus and/or the components thereof (e.g., the moving apparatus).

Further, the moving apparatus may be a robotic apparatus embodied for remote manipulation of the medical object (e.g., a catheter robot). In one embodiment, the moving apparatus is arranged outside the examination object. Further, the moving apparatus may include a fastening element (e.g., movable and/or mobile). Further, the moving apparatus may include a cassette element embodied to record at least part of the medical object. Further, the moving apparatus may include a moving element fastened to the fastening element (e.g., a stand and/or robot arm). Further, the fastening element may be embodied to fasten the moving element to a patient support apparatus. Further, the moving element may include at least one actuator element (e.g., an electric motor), where the providing unit is embodied to control the actuator element. In one embodiment, the cassette element may be coupled (e.g., mechanically and/or electromagnetically and/or pneumatically) to the moving element (e.g., the at least one actuator element). Herein, the cassette element may further include at least one transferring element that may be moved by the coupling between the cassette element and the moving element (e.g., the at least one actuator element). For example, the at least one transferring element may be motion-coupled to the at least one actuator element. In one embodiment, the transferring element is embodied to transfer a movement of the actuator element to the medical object such that the medical object is moved along a longitudinal extension direction of the medical object and/or the medical object is rotated about the longitudinal extension direction. The at least one transferring element may, for example, include a roll and/or roller and/or diaphragm and/or shear plate.

In one embodiment, the moving element may include a plurality of actuator elements (e.g., independently controllable actuator elements). Further, the cassette element may include a plurality of transferring elements (e.g., at least one motion-coupled transferring element) for each of the actuator elements. This may enable movement (e.g., independent and/or simultaneous movement) of the medical object along different degrees of freedom of movement.

The apparatus (e.g., the providing unit) may be embodied to receive the control specification. The reception of the control specification may, for example, include capturing and/or reading a computer-readable data memory and/or reception from a data memory unit (e.g., a database). Further, the control specification may be provided by an input unit for capturing input from an operator. The control specification may include at least one command for control (e.g., step-by-step control) of the moving apparatus. For example, the control specification may include at least one command (e.g., a temporal sequence of commands) for specifying translation and/or rotation (e.g., simultaneous translation and rotation) of the medical object (e.g., the predefined section) by the moving apparatus. In one embodiment, the providing unit may be embodied to translate the control specification and to control the moving apparatus based thereon. Further, the moving apparatus may be embodied to position the medical object based on the control specification (e.g., to move the medical object in a translational and/or rotational manner).

Alternatively or additionally, the control specification may include a specification regarding spatial target positioning to be achieved by the predefined section (e.g., a spatial position and/or alignment and/or pose to be achieved) in the examination object. Herein, the providing unit may be embodied to translate the control specification (e.g., based on a map and/or a model of the examination object) into at least one command for controlling the moving apparatus and to control this thereon. For example, the providing unit may be embodied to control the moving apparatus based on the map and/or the model of the examination object and the control specification such that the predefined section is positioned. For example, the providing unit may be embodied to navigate the predefined section in the examination object using the control specification and the moving apparatus. The examination object may, for example, be a human or animal patient and/or a phantom (e.g., a vascular phantom) and/or a cadaver. For example, the examination object may include a hollow organ (e.g., a vascular section), in which the medical object (e.g., the predefined section) is at least partially arranged.

In one embodiment, the positioning of the predefined section may include a movement (e.g., a translation and/or rotation) of the medical object (e.g., the predefined section) with respect to the moving apparatus (e.g., with respect to the examination object). In one embodiment, after positioning, the predefined section may include an initial positioning (e.g., an initial spatial position and/or alignment and/or pose) in the examination object. Further, the moving apparatus may be embodied to deform the predefined section of the medical object in a defined manner (e.g., using a cable pull) within the medical object. In one embodiment, the apparatus (e.g., the moving apparatus) may be embodied to position the predefined section of the medical object in the initial positioning in the examination object based on the control specification. For example, the control specification may include information with respect to a relative movement of the medical object (e.g., the predefined section) for positioning the predefined section in the initial positioning with respect to the moving apparatus.

Further, the apparatus may be embodied to receive the positioning information on the predefined section. The reception of the positioning information may, for example, include capturing and/or reading a computer-readable data memory and/or reception from a data memory unit (e.g., a database). Further, the positioning information may be received by a capturing unit for capturing a positioning (e.g., instantaneous positioning) of the predefined section. The positioning information may include information on a spatial position and/or alignment and/or pose (e.g. instantaneous) of the predefined section in the examination object.

Further, the apparatus may be embodied to determine the degree of deviation. The degree of deviation describes a deviation between the control specification and the positioning information. For example, the degree of deviation may describe a difference between a spatial target positioning of the predefined section prespecified by the control specification and the actual spatial positioning of the predefined section (e.g., the initial positioning) described by the positioning information. Further, the degree of deviation may include a difference in length (e.g., shortening or lengthening) and/or a difference in angle between the spatial target positioning of the predefined section prespecified by the control specification and the actual positioning described by the positioning information.

If the control specification specifies the spatial positioning of the predefined section with respect to the moving apparatus, the positioning information may describe the spatial positioning (e.g., instantaneous) of the predefined section in, for example, an analogous manner with respect to the moving apparatus. The spatial positioning of the predefined section may, for example, be described by a length dimension along the longitudinal extension direction of the medical object and/or an angle of the medical object relative to the moving apparatus.

Alternatively or additionally, the control specification may specify the spatial positioning of the predefined section with respect to the examination object (e.g., in a patient coordinate system). Here, the positioning information may describe the information on the spatial positioning (e.g., instantaneous) of the predefined section in the same patient coordinate system. The degree of deviation may describe a deviation between the spatial target positioning of the predefined section prespecified by the control specification and the actual spatial positioning described by the positioning information in the patient coordinate system. The deviation between the spatial target positioning of the predefined section prespecified by the control specification and the actual spatial positioning described by the positioning information (e.g., the initial positioning) may be caused by meandering and/or spiraling of the medical object in the hollow organ. Herein, the meandering of the medical object, for example, describes a sinuous course of the medical object, where the sinuous course follows a curvature (e.g., a curve) of the hollow organ mostly on a curve outer side of the hollow organ. Further, rotation of the medical object by the moving apparatus may result in spiraling of the medical object. Herein, the spatial course of the medical object in the hollow organ may include an at least partially spiral-shaped (e.g., spatially twisted) course.

Further, the apparatus may be embodied to determine a correction specification for minimizing the deviation based on the degree of deviation. Herein, the correction specification may (e.g., analogously to the control specification) include at least one command for control (e.g., step-by-step control) of the moving apparatus. For example, the correction specification may include at least one command (e.g., a temporal sequence of commands) for specifying a translation and/or rotation (e.g., simultaneous translation and rotation) of the medical object (e.g., the predefined section) by the moving apparatus. In one embodiment, the apparatus may be embodied to determine the correction specification such that the deviation between the control specification and the positioning information is minimized. For this purpose, the correction specification may include the at least one command for specifying the repositioning of the medical object (e.g., the predefined section). In one embodiment, the moving apparatus may be embodied to reposition the predefined section based on the correction specification from the initial positioning toward the target positioning prespecified by the control specification.

The apparatus may be embodied to repeatedly determine the degree of deviation and/or the correction specification in the event of a change in the positioning information and/or control specification. Further, the moving apparatus may be embodied for repeated repositioning of the predefined section in the event of a changed correction specification.

This enables particularly precise positioning and/or movement of a medical object (e.g., the predefined section)

in the examination object. This may reduce injuries to the examination object. Further, the control of the apparatus (e.g., the moving apparatus) may be improved based on the correction specification. Further, the correction specification may be used for improved path planning for positioning the medical object in a further positioning. For example, the proposed apparatus may compensate and correct incorrect positioning of the predefined section (e.g., due to meandering and/or spiraling) of the medical object in the examination object (e.g., in the hollow organ).

In a further embodiment of the proposed apparatus, the control specification may include a specification for spatial positioning (e.g., a length dimension along the longitudinal extension direction of the medical object and/or an angle of the medical object) and/or a relative movement of the medical object (e.g., the predefined section) with respect to the moving apparatus. Further, the positioning information may include information on the spatial positioning of the predefined section (e.g., the length dimension along the longitudinal extension direction of the medical object and/or the angle of the medical object) with respect to the moving apparatus.

In one embodiment, the control specification may specify the spatial positioning of the medical object (e.g., the predefined section) with respect to the moving apparatus. Herein, the specification for spatial positioning of the medical object (e.g., the predefined section) may include a specification for the length dimension along the longitudinal extension direction of the medical object and/or the angle of the medical object relative to the moving apparatus.

Alternatively or additionally, the control specification may include the specification for the relative movement of the medical object (e.g., the predefined section) with respect to the moving apparatus (e.g., for positioning the predefined section in the initial positioning). Herein, the relative movement may describe a movement (e.g., a translation and/or rotation) of the medical object (e.g., the predefined section) with respect to the moving apparatus.

Further, the positioning information may include information on the spatial positioning (e.g., instantaneous) of the predefined section with respect to the moving apparatus. Herein, the spatial positioning of the predefined section may, for example, be described by the length dimension along the longitudinal extension direction of the medical object and/or the angle of the medical object relative to the moving apparatus.

In one embodiment, the degree of deviation may describe a difference between the spatial positioning prespecified by the control specification and/or the relative movement of the medical object (e.g., the predefined section) with respect to the moving apparatus and the spatial positioning described by the positioning information (e.g., the actual spatial positioning of the predefined section with respect to the moving apparatus). Herein, the degree of deviation may describe a difference in length (e.g., shortening or lengthening) and/or a difference in angle.

In a further embodiment of the proposed apparatus, the apparatus may further be embodied to determine the degree of deviation in dependence on a direction of movement along which the moving apparatus is embodied to position the predefined section.

The at least partial arrangement of the medical object (e.g., elongated medical object) in the examination object (e.g., in a hollow organ of the examination object) may result in meandering and/or spiraling of the medical object. Herein, this meandering and/or spiraling is often dependent on a direction of movement (e.g., translational and/or rotational) for positioning the predefined section.

Herein, the meandering and/or spiraling may be intensified (e.g., maximized) if the predefined section is positioned along a translational direction of movement facing away from the moving apparatus. In contrast, the meandering and/or spiraling may be reduced (e.g., minimized) if the predefined section is positioned along a translational direction of movement facing the moving apparatus. Hence, the deviation between the control specification and the positioning information when the predefined section is positioned along the translational direction of movement facing away from and/or facing the moving apparatus may have a different sign in each case. Further, a manifestation and/or winding direction of the spiraling may be dependent on a rotational direction of movement for positioning the predefined section.

In one embodiment, the apparatus may be embodied to determine the degree of deviation in dependence on the at least one direction of movement (e.g., along a number of different directions of movement), along which the moving apparatus is embodied to position the predefined section. Herein, the apparatus may further be embodied to determine in each case a correction specification for the at least one direction of movement based on the respective degree of deviation for minimizing the associated deviation and to provide the associated deviation to the moving apparatus.

This may enable particularly precise and at the same time efficient correction of incorrect positioning of the predefined section in dependence on the at least one direction of movement for positioning the predefined section.

In a further embodiment of the proposed apparatus, the apparatus may further be embodied to receive a data set including a map and/or a model of the examination object. Herein, the apparatus may moreover be embodied to additionally determine the degree of deviation based on the data set.

The reception of the data set (e.g., the map and/or the model) may, for example, include capturing and/or reading a computer-readable data memory and/or reception from a data memory unit (e.g., a database). Further, the data set may be provided by a providing unit of a medical imaging device for recording and/or providing the data set. The medical imaging device may, for example, include a magnetic resonance imaging system (MRI) and/or a computed tomography system (CT) and/or a medical X-ray device (e.g., a medical C-arm X-ray device) and/or an ultrasound device and/or a positron emission tomography system (PET).

The data set may include a 2D and/or 3D map (e.g., time resolved) of the examination object (e.g., the hollow organ). For example, the data set may include a contrasted and/or segmented map of the examination object (e.g., the hollow organ). Further, the data set may map the examination object preoperatively and/or intraoperatively. Alternatively or additionally, the data set may include a 2D and/or 3D model (e.g., a centerline model and/or a volume model, such as a volume mesh model) of the examination object (e.g., the hollow organ). The data set may be registered with the patient coordinate system and/or with respect to the moving apparatus.

In one embodiment, the apparatus may be embodied to map the initial positioning of the predefined section and/or a spatial course of the medical object in the examination object based on the control specification in the data set. For example, the apparatus may be embodied to determine (e.g., to simulate) the initial positioning of the predefined section and/or the spatial course of the medical object based on the control specification in the data set. In one embodiment, the apparatus may be embodied to simulate and/or map the meandering and/or spiraling of the medical object in the data set when the predefined section is positioned. For this purpose, the apparatus may further be embodied to receive a material parameter and/or operating parameter of the medical object and/or a physiological parameter of the examination object. The reception of the material parameter and/or operating parameter of the medical object and/or the physiological parameter of the examination object may, for example, include capturing and/or reading a computer-readable data memory and/or reception from a data memory unit (e.g., a database). Further, the operating parameter may be provided by the moving apparatus and/or the medical object. Further, the physiological parameter of the examination object may be provided by a sensor unit for capturing the physiological parameter. The sensor unit may, for example, include a respiratory sensor and/or a pulse sensor and/or a motion sensor. The material parameter may, for example, describe a deformability (e.g., extensibility and/or torsional strength and/or flexibility) of the medical object. Further, the operating parameter may describe information on an operating state (e.g., instantaneous) of the medical object. For example, the operating parameter may include information on a spatial pose of the medical object. Further, the physiological parameter may include information on a physiological state and/or a temporal course of the physiological state of the examination object (e.g., during the positioning of the predefined section). The physiological parameter may, for example, include a respiratory signal and/or a pulse signal and/or a motion signal of the examination object. In one embodiment, the apparatus may be embodied to simulate the initial positioning of the predefined section and/or the spatial course of the medical object additionally based on the material parameter and/or the operating parameter of the medical object and/or the physiological parameter of the examination object in the data set. This may enable the meandering and/or spiraling of the medical object in the examination object (e.g., in the hollow organ) to be simulated and/or mapped particularly precisely in the data set.

The inclusion of the data set when determining the degree of deviation enables the spatial course (e.g., the meandering and/or spiraling) of the medical object in the examination object to be taken into account. For example, the data set may include information on a spatial course and/or a spatial extent of the hollow organ, in which the medical object is at least partially arranged (e.g., a diameter and/or a cross-sectional area). The apparatus may be embodied to determine the degree of deviation particularly precisely (e.g., in dependence on the direction of movement for positioning the predefined section) additionally based on the data set. Herein, the apparatus may further be embodied to take into account the information on the spatial course and/or the spatial extent of the hollow organ for determining the degree of deviation (e.g., a difference in length and/or difference in angle) in dependence on the direction of movement for positioning the predefined section.

In a further embodiment of the proposed apparatus, the data set may include a centerline model of a vascular section of the examination object. Herein, the predefined section may be arranged in the vascular section. Further, the apparatus may be embodied to determine the deviation with respect to the centerline model.

The centerline model may include at least one centerline. The centerline describes the spatial course of the hollow organ (e.g., at least one vascular section of the examination object) spatially (e.g., two-dimensionally and/or three-dimensionally). Herein, the at least one centerline may be a midline of the hollow organ, which in each case, extends along a longitudinal extension direction of the hollow organ through the midpoint of the cross-sectional area of the hollow organ. For example, the apparatus may be embodied to determine (e.g., to simulate) the initial positioning of the predefined section and/or the spatial course of the medical object based on the control specification in the centerline model.

Herein, a spatial course of the at least one centerline from an entry point of the medical object into the examination object to a spatial target positioning of the predefined section may describe a mean distance of the medical object (e.g., if the medical object were to be arranged along the centerline). When positioning the predefined section along a direction (e.g., translational direction) of movement facing away from the moving apparatus, meandering and/or spiraling of the medical object in the hollow organ may result in a lengthening of the distance from the entry point to the target positioning compared to the mean distance. Further, when the predefined section is positioned along a direction (e.g., translational direction) of movement facing the moving apparatus, there may be a shortening of the distance from the entry point to the target positioning compared to the mean distance. In one embodiment, the apparatus may be embodied to determine the deviation (e.g., the degree of deviation) with respect to the centerline model (e.g., the mean distance). Herein, the apparatus may further be embodied to determine the shortening and/or lengthening of the distance from the entry point to the target positioning compared to the mean distance by determining (e.g., section-by-section) a spatial deviation between the spatial course of the medical object and the centerline model (e.g., substantially perpendicular to the at least one centerline). Herein, the spatial deviation between the spatial course of the medical object and the centerline model may be limited by the spatial extent of the hollow organ (e.g., a diameter and/or a cross-sectional area).

Further, the apparatus may be embodied to additionally determine the correction specification for minimizing the deviation based on the course of the at least one centerline. Further, the apparatus may be embodied to take account of a curvature and/or spatial extent of the hollow organ for the determination of the correction specification.

This may enable particularly precise correction of incorrect positioning of the predefined section (e.g., taking into account the spatial course of the medical object in the hollow organ).

In a further embodiment of the proposed apparatus, the moving apparatus may be embodied to move the medical object for positioning the predefined section in an initial positioning along a first direction of movement based on the control specification. Further, the moving apparatus may be embodied to move the medical object based on a further control specification such that the predefined section starts to leave an initial positioning. Further, the apparatus may be embodied to additionally determine the degree of deviation based on a comparison of the control specification with the further control specification.

Herein, the first direction of movement may substantially face toward or face away from the moving apparatus. In one embodiment, the apparatus may be embodied to capture a deviation of the predefined section from the initial positioning (e.g., a change in the positioning). For example, the apparatus may be embodied to capture the change in positioning of the predefined section based on the positioning information (e.g., a change in the positioning information).

The further control specification may, for example, include all the features and properties as described in relation to the control specification and vice versa. Further, the moving apparatus may be embodied to move the medical object based on the further control specification against the first direction of movement such that a positioning (e.g., instantaneous) of the predefined section deviates from the initial positioning. For example, the moving apparatus may be embodied to move the medical object according to the further control specification against the first direction of movement until the predefined section starts to leave an initial positioning. Herein, the further control specification may include information with respect to a relative movement of the medical object (e.g., the predefined section) with respect to the moving apparatus, where the relative movement includes a period of time of the movement of the medical object against the first direction of movement from the start of the movement up to a point in time at which the predefined section starts to leave its initial positioning. For example, the further control specification may include information regarding a spatial distance covered during the relative movement of the medical object with respect to the moving apparatus and/or an angle of rotation (e.g., up to the point in time at which the predefined section deviates from an initial positioning).

After the predefined section has been positioned in the initial positioning in the examination object (e.g., the hollow organ), the spatial course of the medical object may include a lengthening (e.g., compared to the mean distance) along a first direction of movement facing away from the moving apparatus (e.g., due to meandering and/or spiraling of the medical object). Herein, the moving apparatus may be embodied to shorten this lengthening by moving the medical object against the first direction of movement (e.g., along a direction of movement facing the moving apparatus). Alternatively, after the predefined section has been positioned in the initial positioning in the examination object (e.g., the hollow organ), the spatial course of the medical object may include a shortening (e.g., compared to the mean distance) along a first direction of movement facing the moving apparatus. Herein, the moving apparatus may be embodied to lengthen this shortening by moving the medical object against the first direction of movement (e.g., along a direction of movement facing away from the moving apparatus).

The apparatus may further be embodied to additionally determine the degree of deviation based on the comparison of the control specification with the further control specification. The comparison of the control specification with the further control specification may, for example, include a formation of a difference of the translation and/or rotation of the medical object prespecified by the respective control specification with respect to the moving apparatus. Herein, the apparatus may be embodied to determine the degree of deviation (e.g., including a difference in length and/or difference in angle of the medical object) with respect to the initial positioning (e.g., between the maximum shortening and maximum lengthening of the arrangement of the medical object in the hollow organ). This enables it to be provided that, on a movement of the medical object (e.g., against the first direction of movement), according to a second control specification, the predefined section follows this specification directly and without delay. Further, the apparatus may be embodied to determine the correction specification based on the degree of deviation (e.g., based on the further control specification).

According to a further embodiment, the apparatus may be embodied to move the medical object repeatedly, based on the further control specification, in each case one after the other along two opposite directions of movement (e.g., in an oscillatory manner). In one embodiment, a distance of the movement (e.g., the translation and/or rotation) may in each case be the same for the opposing movements of the medical object in a repetition so that, after an oscillation, the medical object is in each case again arranged in an original positioning. Further, the apparatus may be embodied to increase the amplitude of the movement (e.g., the oscillation) with each repetition of the paired opposing movement of the medical object until the predefined section starts to leave an initial positioning. This enables the apparatus to be embodied to determine the degree of deviation and/or the correction specification for the opposing directions of movement based on the further control specification and the amplitude of the movement at the point in time of the leaving of the initial positioning of the predefined section. In one embodiment, the apparatus may further be embodied to determine the degree of deviation and/or the correction specification by moving the medical object in an oscillatory manner along two opposing directions of rotation and/or along two opposing directions of translation at the initial positioning. This enables the apparatus to be embodied to ascertain and provide the correction specification for the different degrees of freedom of movement of the moving apparatus (e.g., the medical object) in a particularly precise manner. Further, the oscillatory movement may provide that the predefined section is arranged in the initial positioning after each repetition.

In a further embodiment of the proposed apparatus, the apparatus may further be embodied to determine the degree of deviation and the correction specification for different initial positionings of the predefined section in the examination object. Further, the apparatus may be embodied to determine the correction specification for at least one further positioning of the predefined section in the examination object by interpolation and/or extrapolation of the correction specifications determined so far.

In one embodiment, the apparatus (e.g., the moving apparatus) may be embodied to position the predefined section of the medical object (e.g., one after the other) at different initial positionings in the examination object (e.g., the hollow organ). Herein, the different initial positionings may form a path in the examination object (e.g., the hollow organ). For example, the moving apparatus may be embodied to move the predefined section of the medical object along the path toward the target positioning. Herein, the apparatus may be embodied to determine the degree of deviation and the correction specification for each of the different initial positionings (e.g., along the path). Moreover, the apparatus may be embodied to determine the degree of deviation and the correction specification for the different initial positionings in each case according to one of the above-described embodiments. Further, the apparatus may be embodied to determine the correction specification for at least one further positioning of the predefined section (e.g., for intermediate positionings along the path and/or for the target positioning) by interpolation and/or extrapolation of the correction specifications determined so far. For example, the apparatus may be embodied, based on the degrees of deviation and correction specifications determined for the different initial positionings, to parameterize the degree of deviation and/or the correction specification in dependence on the control specification for positioning the predefined section. This may, for example, take place under the assumption that the degree of deviation and/or the correction specification is dependent on a length of the part of the medical object arranged in the examination object. This enables the apparatus to be embodied to determine the correction specification for the control specification for positioning the predefined section (e.g., in the target positioning) by extrapolation and/or interpolation of the correction specifications determined so far. This may enable particularly precise and at the same time efficient positioning of the predefined section (e.g., taking into account the path along which the predefined section is moved toward the target positioning).

In a further embodiment of the proposed apparatus, the apparatus may be embodied to determine the positioning information by applying a trained function to the control specification. Herein, at least one parameter of the trained function may be based on a comparison of training positioning information with comparison positioning information.

The trained function may be trained by a machine learning method. For example, the trained function may be a neural network (e.g., a convolutional neural network (CNN) or a network including a convolutional layer). Further, the trained function may be embodied to process the control specification as input data and to provide the positioning information as output data.

The trained function maps input data to output data. The output data may, for example, also depend on one or more parameters of the trained function. The one or more parameters of the trained function may be determined and/or adjusted by training. The determination and/or the adjustment of the one or more parameters of the trained function may, for example, be based on a pair consisting of training input data and associated training output data, where the trained function is applied to the training input data to generate training mapping data. For example, the determination and/or the adjustment may be based on a comparison of the training mapping data and the training output data. In general, a trainable function (e.g., a function with one or more parameters that have not yet been adjusted) is also referred to as a trained function.

Other terms for trained function are trained mapping rule, mapping rule with trained parameters, function with trained parameters, algorithm based on artificial intelligence, and machine learning algorithm. An example of a trained function is an artificial neural network, where the edge weights of the artificial neural network correspond to the parameters of the trained function. Instead of the term "neural network", it is also possible to use the term "neural net". For example, a trained function may also be a deep neural network or deep artificial neural network. A further example of a trained function is a "support vector machine"; further, other machine learning algorithms may also be used as the trained function.

The trained function may, for example, be trained by back propagation. First, training mapping data may be determined by applying the trained function to training input data. Thereafter, a deviation between the training mapping data and the training output data may be ascertained by applying an error function to the training mapping data and the training output data. Further, at least one parameter (e.g., a weighting) of the trained function (e.g., the neural network) may be iteratively adjusted based on a gradient of the error function with respect to the at least one parameter of the trained function. This enables minimization of the deviation between the training mapping data and the training output data during the training of the trained function.

In one embodiment, the trained function (e.g., the neural network) includes an input layer and an output layer. Herein, the input layer may be embodied to receive input data. Further, the output layer may be embodied to provide mapping data. Herein, the input layer and/or the output layer may in each case include a plurality of channels (e.g., neurons).

The input data of the trained function may be formed by the control specification. Further, the output data of the trained function may be formed by the positioning information.

In one embodiment, the at least one parameter of the trained function may be based on a comparison between training positioning information and comparison positioning information. Herein, the training positioning information and/or the comparison positioning information may have been determined as part of a proposed computer-implemented method for providing a trained function, which will be explained in the further course of the description. For example, the trained function may be provided by an embodiment of the proposed computer-implemented method for providing a trained function.

Further, the input data of the trained function may additionally be based on the material parameter and/or the operating parameter of the medical object and/or the physiological parameter of the examination object. Further, the input data of the trained function may be based on the data set (e.g., the centerline model) of the examination object and/or the medical image data.

The application of the trained function to the control specification enables the positioning information to be determined efficiently (e.g., without a capturing unit for capturing the positioning of the predefined section).

In a second aspect, the present embodiments relate to a system including an apparatus according to the present embodiments and a capturing unit. Herein, the capturing unit is embodied to capture the positioning and/or change in positioning of the predefined section in the examination object. Further, the capturing unit is embodied to determine the positioning information based on the captured positioning and/or change in positioning and to provide the positioning information to the apparatus.

The capturing unit may include a sensor (e.g., an electromagnetic and/or optical and/or acoustic, such as ultrasound-based, and/or gyroscopic sensor) embodied to detect the predefined section. For this purpose, the medical object (e.g., the predefined section) may, for example, include a marker structure that may be captured (e.g., identified and/or localized by the capturing unit). The capturing unit may, for example, be arranged in and/or on the medical object (e.g., the predefined section). For example, the capturing unit may be at least partially arranged integrated in the medical object (e.g., the predefined section). Alternatively or additionally, the capturing unit may be arranged spatially spaced apart from the medical object. The capturing unit may include a capturing area that at least partially includes a volume of the examination object (e.g., the hollow organ), in which the medical object (e.g., the predefined section) is at least partially arranged. Herein, the capturing unit may be embodied to capture the positioning (e.g., instantaneous; a spatial position and/or alignment) of the predefined section. Further, the capturing unit may be embodied to capture a change in positioning of the predefined section. For example, the capturing unit may be embodied to capture a deviation of the predefined section from an initial positioning. For example, the capturing unit may be embodied to determine the positioning and/or change in positioning of the predefined section with respect to a reference positioning (e.g., the initial positioning) and/or absolutely (e.g., with respect to the patient coordinate system). For this purpose, a coordinate system of the capturing unit may be registered with the patient coordinate system and/or with respect to the moving apparatus.

The capturing unit may further be embodied to provide the positioning information to the apparatus based on the captured positioning and/or change in positioning of the predefined section. The provision of the positioning information may, for example, include storage on a computer-readable storage medium and/or displaying on a depicting unit and/or transmission to the providing unit.

The proposed embodiment enables the positioning information to be recorded precisely (e.g., independently of the control specification). This enables the actual positioning and/or change in positioning of the predefined section to be used to determine the degree of deviation and the correction specification.

In a further embodiment of the proposed system, the capturing unit may include a medical imaging device embodied to record medical image data of the examination object. Herein, the predefined section in the medical image data may be mapped in a time-resolved manner (e.g., intraoperatively). Further, the capturing unit may be embodied to capture the positioning and/or change in positioning of the predefined section based on the medical image data.

The medical imaging device may, for example, include a magnetic resonance imaging system (MRI) and/or a computed tomography system (CT) and/or a medical X-ray device (e.g., a medical C-arm X-ray device), and/or an ultrasound device, and/or a positron emission tomography system (PET). The medical imaging device may be embodied to record the medical image data of the examination object. Herein, the medical image data may include a 2D and/or 3D map (e.g., a time-resolved map) of the examination object (e.g., the hollow organ and/or the predefined section). For example, the medical image data may map a movement of the predefined section in the examination object (e.g., the hollow organ) in a time-resolved manner. In one embodiment, the capturing unit (e.g., the medical imaging device) may be embodied to identify and/or localize the predefined section in the medical image data. Further, the capturing unit (e.g., the medical imaging device) may be embodied to determine the positioning and/or change in positioning of the predefined section based on the medical image data in a time-resolved manner. For this purpose, the capturing unit (e.g., the medical imaging device) may further be embodied to segment the predefined section in the medical image data. Further, the capturing unit (e.g., the medical imaging device) may be embodied to determine the positioning and/or change in positioning of the predefined section with respect to a reference map from the medical image data and/or absolutely (e.g., with respect to the patient coordinate system). For this purpose, a coordinate system of the medical imaging device (e.g., the medical image data) may be registered with the patient coordinate system and/or with respect to the moving apparatus. The capturing unit (e.g., the medical imaging device) may further be embodied to determine the positioning information based on the positioning and/or change in positioning of the predefined section captured based on the medical image data and provide the positioning information to the apparatus.

The proposed embodiment enables precise (e.g., image-based) capturing of the positioning information (e.g., independently) of the control specification. This enables the actual positioning and/or change in positioning of the predefined section to be used to determine the degree of deviation and the correction specification.

In a third aspect, the present embodiments relate to a method for providing a correction specification. Herein, in a first act a), a control specification is received by an apparatus (e.g., an apparatus according to the present embodiments) for positioning a medical object. Further, the apparatus includes a moving apparatus for robotically moving the medical object. Further, the medical object includes a predefined section, where the predefined section is at least partially arranged in an examination object. Further, prior to the start of the method, the predefined section has been positioned by the moving apparatus based on the control specification. In a second act b), positioning information on the predefined section of the medical object is received. In a third act c), a degree of deviation is determined, where the degree of deviation describes a deviation between the control specification and the positioning information. Further, in a fourth act d), the correction specification for minimizing the deviation is determined based on the degree of deviation. In a fifth act e), the correction specification is provided.

The advantages of the proposed method for providing a correction specification substantially correspond to the advantages of the proposed apparatus for positioning a medical object and/or the proposed system. Features, advantages or alternative embodiments mentioned herein may likewise be transferred to the other subject matter and vice versa.

In one embodiment, the proposed method (e.g., acts a) to e)) may be executed after the predefined section of the medical object has been positioned (e.g., in the initial positioning).

The reception of the control specification and/or the positioning information may, for example, include capturing and/or reading a computer-readable data memory and/or reception from a data memory unit (e.g., a database). Further, the control specification may be provided by a proposed apparatus and/or a proposed system and/or an input unit for capturing input from an operator. Further, the positioning information may be provided by a proposed apparatus (e.g., a capturing unit) and/or a proposed system.

The control specification and/or the positioning information may, for example, include all the properties and features as described in relation to the apparatus for positioning a medical object and vice versa.

The provision of the correction specification in act e) may, for example, include storage on a computer-readable storage medium and/or displaying on a depicting unit and/or transfer to a providing unit. The correction specification provided may support an operator in the correction of possible incorrect positioning of the predefined section.

In a further embodiment of the proposed method, the control specification may include a specification for spatial positioning (e.g., a length dimension along the longitudinal extension direction of the medical object and/or an angle of the medical object) and/or a relative movement of the medical object (e.g., the predefined section) with respect to the moving apparatus. Further, the positioning information may include information on the spatial positioning of the predefined section (e.g., the length dimension along the longitudinal extension direction of the medical object and/or the angle of the medical object) with respect to the moving apparatus.

In a further embodiment of the proposed method, the control specification may include information on a direction of movement, where, prior to the start of the method, the predefined section has been positioned along the direction of movement by the moving apparatus. Further, the degree of deviation in act c) may be determined in dependence on the direction of movement.

In one embodiment, the control specification received in act a) may include information on the direction of movement along which the predefined section was positioned by the moving apparatus.

The meandering and/or spiraling of the medical object within the examination object is frequently dependent on the direction of movement (e.g., translational and/or rotational) for positioning the predefined section. If the predefined section has been positioned by the moving apparatus along a translational direction of movement facing away from the moving apparatus, the meandering and/or spiraling may be intensified (e.g., maximized). If the predefined section has been positioned by the moving apparatus along a translational direction of movement facing the moving apparatus, the meandering and/or spiraling may be reduced (e.g., minimized). Hence, the deviation between the control specification and the positioning information may have a different sign in each case in dependence on the direction of movement (e.g., with respect to the moving apparatus) for the positioning of the predefined section. Further, a manifestation and/or winding direction of the spiraling may be dependent upon a rotational direction of movement for positioning the predefined section.

In one embodiment, the degree of deviation may be determined in dependence on the at least one direction of movement (e.g., along a number of different directions of movement), along which the predefined section was positioned by the direction of movement. Further, in each case, a correction specification for minimizing the associated deviation of the at least one direction of movement may be determined based on the respective degree of deviation. This enables the intensification or reduction in the meandering and/or spiraling of the medical object in dependence on the direction of movement to be taken into account for the determination of the degree of deviation and the correction specification.

In a further embodiment of the method for providing a correction specification, the method may also include act a.2), where a data set including a map and/or a model of the examination object may be received. Herein, the degree of deviation may be determined in act c) based on the data set and the positioning information.

The reception of the data set (e.g., the map and/or the model) may, for example, include capturing and/or reading a computer-readable data memory and/or reception from a data memory unit (e.g., a database). Further, the data set may be provided by a providing unit of the medical imaging device for recording and/or providing the data set. The data set may, for example, include all the properties and features as described in relation to the apparatus for positioning a medical object and vice versa.

When the predefined section has been positioned by the moving apparatus prior to the start of the proposed method, the initial positioning and/or a spatial course of the medical object, which is at least partially arranged in the examination object, may be mapped in the data set based on the control specification. Herein, the initial positioning of the predefined section and/or the spatial course of the medical object may be determined (e.g., simulated) based on the control specification in the data set. In one embodiment, the meandering and/or spiraling of the medical object may be simulated and/or mapped in the data set. For this purpose, in act a.2), further a material parameter and/or an operating parameter of the medical object and/or a physiological parameter of the examination object may be received. The reception of the material parameter and/or operating parameter of the medical object and/or the physiological parameter of the examination object may, for example, include capturing and/or reading a computer-readable data memory and/or reception from a data memory unit (e.g., a database). Further, the operating parameter may be provided by the moving apparatus and/or the medical object. Further, the physiological parameter of the examination object may be provided by a sensor unit for capturing the physiological parameter. Further, the material parameter and/or the operating parameter of the medical object and/or the physiological parameter of the examination object may include all the properties and features as described in relation to the apparatus for positioning a medical object and vice versa.

In one embodiment, the initial positioning of the predefined section and/or the spatial course of the medical object may also be simulated in the data set based on the material parameter and/or the operating parameter of the medical object and/or the physiological parameter of the examination object. This enables the meandering and/or spiraling of the medical object in the examination object (e.g., in the hollow organ) to be simulated and/or mapped particularly precisely in the data set. Further, the degree of deviation (e.g., in dependence on the direction of movement along which the predefined section was positioned prior to the start of the method) may additionally be determined particularly precisely based on the data set. In one embodiment, herein, the information contained in the data set on the spatial course and/or the spatial extent of the hollow organ may be taken into account for the determination of the degree of deviation (e.g., a difference in length and/or difference in angle) in dependence on the direction of movement.

In a further embodiment of the method for providing a correction specification, the data set may include a centerline model of a vascular section of the examination object. Herein, the predefined section may be arranged in the vascular section. Further, the degree of deviation may be determined in act c) with respect to the centerline model.

The centerline model may, for example, include all the properties and features as described in relation to the apparatus for positioning a medical object and vice versa. Further, the initial positioning of the predefined section and/or the spatial course of the medical object may be determined (e.g., simulated) based on the control specification in the centerline model. Further, a spatial course of the at least one centerline of the centerline model from an entry point of the medical object into the examination object to the spatial target positioning of the predefined section may describe a mean distance of the medical object (e.g., if the medical object were to be arranged along the centerline). If the predefined section was positioned along a direction of movement facing away from the moving apparatus, the meandering and/or spiraling of the medical object in the hollow organ may result in a lengthening of the distance from the entry point to the target position compared to the mean distance. Similarly, there may be a shortening of the distance from the entry point to the target positioning compared to the mean distance if the predefined section was positioned along a direction of movement facing the moving apparatus. In one embodiment, the deviation (e.g., the degree of deviation) may be determined in act c) with respect to the centerline model (e.g., with respect to the mean distance). For example, the shortening and/or lengthening of the distance from the entry point to the target position compared to the mean distance may be determined by determining (e.g., section-by-section) the spatial deviation between the spatial course of the medical object and the centerline model (e.g., substantially perpendicular to the at least one centerline). Herein, the spatial deviation between the spatial course of the medical object and the centerline model (e.g., the at least one centerline) may be limited by the spatial extent of the hollow organ (e.g., a diameter and/or a cross-sectional area). For this purpose, the data set may include information regarding the diameter and/or the cross-sectional area of the hollow organ along the at least one centerline.

Further, the medical object may include a spatial course in the hollow organ, where the meandering and/or spiraling may cause an at least section-by-section shortening and an at least section-by-section lengthening of the distance from the entry point to the target positioning compared to the mean distance. Herein, the spatial course of the medical object may deviate from the centerline, where the at least section-by-section shortening and lengthening of the distance from the entry point to the target positioning compared to the mean distance may lead to an at least partial compensation of the difference in length. For this purpose, i the degree of deviation with respect to the centerline model may be determined.

Moreover, the correction specification for minimizing the deviation may also be determined based on the course of the at least one centerline. Here, a curvature and/or spatial extent of the hollow organ may be taken into account for the determination of the correction specification.

This enables particularly precise correction of incorrect positioning of the predefined section (e.g., taking into account the spatial course of the medical object in the hollow organ).

In a further embodiment of the proposed method for providing a correction specification, the method may also include act a.3), where a further control specification is received by the apparatus. Herein, prior to the start of the method, the medical object may have been moved by the moving apparatus for the initial positioning of the predefined section along a first direction of movement based on the control specification. Further, prior to the start of the method, the medical object may have been moved by the moving apparatus based on the further control specification against the first direction of movement such that the predefined section deviates from an initial positioning. In one embodiment, thereafter, the degree of deviation may be determined in act c) based on a comparison of the control specification with the further control specification.

The reception of the further control specification may, for example, include capturing and/or reading a computer-readable data memory and/or reception from a data memory unit (e.g., a database). Further, the further control specification may be provided by an input unit for capturing input from an operator. The further control specification may, for example, include all the features and properties as described in relation to the control specification and/or in relation to the apparatus for positioning a medical object and vice versa.

The first direction of movement may substantially face toward or away from the moving apparatus. In one embodiment, the deviation of the predefined section from an initial positioning (e.g., a change in positioning) may have been captured based on the positioning information (e.g., based on a change in the positioning information).

The meandering and/or spiraling of the medical object at least partially arranged in the examination object may be reduced (e.g., minimized) or intensified (e.g., maximized in dependence on the first direction of movement). Consequently, after the predefined section has been positioned in an initial positioning by the moving apparatus, the spatial course of the medical object may include a lengthening or shortening compared to the mean distance. Due to the fact that, prior to the start of the method, the medical object has been moved by the moving apparatus based on the further control specification against the first direction of movement, herein, the above-described lengthening was shortened or the above-described shortening was lengthened. For example, herein the state of the spatial course of the medical object that has been lengthened or shortened compared to the mean distance was reversed into a spatial course that is shortened or lengthened compared to the mean distance.

In one embodiment, the degree of deviation may additionally be determined based on the comparison of the control specification with the further control specification. The comparison of the control specification with the further control specification may, for example, include the formation of a difference of the translation and/or rotation of the medical object prespecified by the respective control specification with respect to the moving apparatus. Herein, the degree of deviation (e.g., including a difference in length and/or difference in angle of the medical object) may be determined with respect to the initial positioning (e.g., between the maximum shortening and maximum lengthening of the arrangement of the medical object in the hollow organ). Herein, the degree of deviation, for example, describes the difference in length and/or difference in angle that is to be compensated during a movement of the medical object along the direction of movement opposite to the first direction of movement before the predefined section would deviate from an initial positioning. Herein, the correction specification may be determined based on the degree of deviation (e.g., based on the further control specification). For example, the degree of deviation describes a slippage of the spatial arrangement of the medical object in the hollow organ, which may be determined and provided as a correction specification (e.g., in dependence on the direction of movement).

The above-described embodiment of the proposed method enables a particularly precise determination of the degree of deviation and the correction specification that was ascertained (e.g., verified) by the movement of the medical object against the first direction of movement that took place prior to the start of the method.

In a further embodiment of the proposed method for providing a correction specification, in act a), a plurality of control specifications for different initial positionings of the predefined section in the examination object may be received. Further, in act a.3), a plurality of further control specifications for the initial positionings of the predefined section may be received. Herein, the degree of deviation and the correction specification for the different initial positionings in the examination object may be determined. Further, the correction specification may be determined for at least one further possible positioning of the predefined section in the examination object by interpolation and/or extrapolation of the correction specifications determined so far.

The different initial positionings of the predefined section may form a path in the examination object (e.g., the hollow organ). For example, prior to the start of the method, the predefined section of the medical object may have been moved by the moving apparatus along the path toward the target positioning. In one embodiment, the degree of deviation and the correction specification for the different initial positionings (e.g., along the path) may be determined. For example, the degree of deviation and the correction specification for the different initial positionings may, in each case, be determined according to one of the above-described embodiments (e.g., by a comparison of the in each case mutually corresponding control specifications and further control specifications). Further, the correction specification may be determined for at least one further possible positioning of the predefined section (e.g., for a possible intermediate positioning along the path and/or for the target positioning) by interpolation and/or extrapolation of the correction specifications determined so far. The at least one further possible positioning may, for example, be specified by an operator input using the input unit. For example, the degree of deviation and/or the correction specification may be parameterized in dependence on the control specification based on the degrees of deviation and correction specifications determined for the different initial positionings. This enables the correction specification for the control specification for positioning the predefined section (e.g., in the target positioning) to be determined and provided by extrapolation and/or interpolation of the correction specifications determined so far.

The above-described embodiment of the proposed method enables a particularly precise determination of the degree of deviation and the correction specification (e.g., taking into account the path along which the predefined section was moved toward the target positioning prior to the start of the method) by the moving apparatus.

According to a further embodiment of the proposed method, in act a), a plurality of control specifications for the different initial positionings of the predefined section in the examination object may be received. Further, in act b), a plurality of items of positioning information on the initial positionings of the predefined section may be received. Herein, the degree of deviation and the correction specification for the different initial positionings in the examination object may in each case be determined according to one of the above-described embodiments. Further, the correction specification for the at least one further possible positioning of the predefined section in the examination object may be determined by interpolation and/or extrapolation of the correction specifications determined so far.

In a further embodiment of the proposed method for providing a correction specification, the positioning information may be determined in act b) by applying a trained function to the control specification. Herein, at least one parameter of the trained function may be based on a comparison of training positioning information with comparison positioning information.

The trained function and/or the training positioning information and/or the comparison positioning information may, for example, include all the features and properties as described in relation to the apparatus for positioning a medical object and vice versa. For example, the trained function may be provided by an embodiment of the proposed method for providing a trained function.

Hence, the control specification may form the input data of the trained function. Further, the positioning information may form the output data of the trained function.

Further, the input data of the trained function may also be based on the material parameter and/or the operating parameter of the medical object and/or the physiological parameter of the examination object. Further, the input data of the trained function may be applied to the data set (e.g., the centerline model) of the examination object and/or the medical image data.

The application of the trained function to the control specification enables an efficient determination of the positioning information (e.g., without a capturing unit for capturing the positioning of the predefined section).

In a further embodiment of the proposed method for providing a correction specification, the method may also include act b.0), where medical image data of the examination object is received. Herein, the predefined section may be mapped in the medical image data in a time-resolved manner. Further, the positioning information may be determined in act b) based on the medical image data.

The reception of the medical image data may, for example, include capturing and/or reading a computer-readable data memory and/or reception from a data memory unit (e.g., a database). Further, the medical image data may be provided by the medical imaging device for recording the medical image data. The medical image data may, for example, include all the properties and features as described in relation to the apparatus for positioning a medical object and vice versa.

In one embodiment, the predefined section of the medical object may be identified and/or localized in the medical image data. Further, the positioning and/or change in positioning of the predefined section may be determined based on the medical image data in a time-resolved manner. For this purpose, the predefined section may be segmented in the medical image data. Further, the positioning and/or change in positioning of the predefined section with respect to a reference map may be determined from the medical image data and/or absolutely (e.g., with respect to the patient coordinate system). For this purpose, a coordinate system of the medical imaging device (e.g., the medical image data) may be registered with the patient coordinate system and/or with respect to the moving apparatus. Further, the positioning information may be determined in act b) based on the positioning and/or change in positioning of the predefined section mapped in the medical image data in a time-resolved manner.

The proposed embodiment enables a precise determination of the positioning information of the predefined section (e.g., independently of the control specification).

In a fourth aspect, the present embodiments relate to a method (e.g., computer-implemented) for providing a trained function. Herein, in a first act t1), training control specifications are received by an apparatus for positioning a medical object. Further, in a second act t2), in each case, comparison positioning information for each of the training control specifications for a predefined section of the medical object is received. In a third act t3), training positioning information is determined by applying the trained function to the training control specifications. In a fourth act t4), at least one parameter of the trained function is adjusted based on a comparison of the training positioning information with the comparison positioning information. Further, the trained function is provided in a fifth act t5).

The reception of the training control specifications in act t1) and/or the reception of the comparison positioning information in act t2) may, for example, include capturing and/or reading a computer-readable data memory and/or reception from a data memory unit (e.g., a database). Further, the training control specification may be provided by an input unit for capturing input from an operator and/or a proposed apparatus for positioning a medical object. Further, the comparison positioning information may be provided by a capturing unit (e.g., a medical imaging device) for capturing a positioning and/or change in positioning of the predefined section of the medical object.

The training control specifications may, for example, include all the properties of the control specification as described in relation to the apparatus for positioning a medical object and/or in relation to the method for providing a correction specification and vice versa. Further, the comparison positioning information may include all the properties of positioning information described in relation to the apparatus for positioning a medical object and/or in relation to the method for providing a correction specification and vice versa. Further, the training control specifications and/or the comparison positioning information may be simulated.

In one embodiment, in act t1), a plurality of training control specifications (e.g., different training control specifications) for at least one examination object (e.g., different examination objects) may be received. Further, in act t2), in each case, comparison positioning information on each of the training control specifications may be received. Herein, the comparison positioning information may in each case include information on the spatial positioning and/or change in positioning of the predefined section, where, prior to the start of the method, the predefined section has been positioned (e.g., in a simulated manner) by the moving apparatus based on the respective training control specification. In one embodiment, the comparison positioning information may in each case describe the actual positioning of the predefined section.

In act t3), training positioning information may be determined by applying the trained function to the training control specifications. In other words, the training control specifications may form the input data of the trained function, and the training positioning information may form the output data of the trained function. Further, the input data of the trained function may be based on the material parameter and/or the operating parameter of the medical object and/or the physiological parameter of the examination object as described in relation to the method for providing a correction specification. Further, the input data of the trained function may be based on a data set (e.g., a centerline model) of the examination object and/or the medical image data as described in relation to the method for providing a correction specification.

In act t4), the at least one parameter of the trained function may be adjusted based on the comparison of the training positioning information with the comparison positioning information. Herein, the comparison may, for example, include a determination of a difference in length and/or difference in angle between mutually corresponding items of training positioning information in each case based on the training control specification and comparison positioning information. In one embodiment, the at least one parameter may be adjusted such that a deviation between the comparison positioning information and training positioning information is minimized.

The provision of the trained function in act t5) may, for example, include storage on a computer-readable storage medium and/or transfer to a providing unit (e.g., to a proposed apparatus for positioning a medical object).

In one embodiment, the proposed method may provide a trained function that may be used in one embodiment of the apparatus for positioning the medical object and/or the method for providing a correction specification.

The present embodiments may further relate to a providing unit including a computing unit, a memory unit, and an interface. Herein, the providing unit may be embodied to execute an embodiment of the proposed method for providing a correction specification in that the components of the providing unit are embodied to execute the individual method acts. For example, the interface may be embodied to execute acts a) (e.g., the further subacts a.1) to a.3)), b) (e.g., the further subact b.0)), and/or e). Further, the computing unit and/or the memory unit may be embodied to execute the other acts.

The advantages of the proposed providing unit substantially correspond to the advantages of the proposed method for providing a correction specification. Features, advantages, or alternative embodiments mentioned here may likewise also be transferred to the other subject matter and vice versa.

The present embodiments may further relate to a training unit including a training computing unit, a training memory unit, and a training interface. Herein, the training unit may be embodied to execute an embodiment of the proposed method for providing a trained function in that the components of the training unit are embodied to execute the individual method acts. For example, the training interface may be embodied to execute acts t1), t2), and/or t5). Further, the training computing unit and/or the training memory unit may be embodied to execute acts t3) and t4).

The advantages of the proposed training unit substantially correspond to the advantages of the proposed method for providing a trained function. Features, advantages, or alternative embodiments may likewise be transferred to the other subject matter and vice versa.

In a fifth aspect, the present embodiments relate to a computer program product with a computer program that may be loaded directly into a memory of a providing unit, with program sections for executing all the acts of the computer-implemented method for providing a correction specification and/or one of the aspects thereof when the program sections are executed by the providing unit. Alternatively or additionally, the computer program product may include a computer program that may be loaded directly into a training memory of a training unit with program sections for executing all the acts of the proposed method for providing a trained function and/or one of the aspects thereof when the program sections are executed by the training unit.

The present embodiments may further relate to a computer-readable storage medium on which program sections that may be read and executed by a providing unit are stored for executing all the acts of the method for providing a correction specification and/or one of the aspects thereof when the program sections are executed by the providing unit. Alternatively or additionally, the computer-readable storage medium may store program sections that may be read and executed by a training unit to execute all the acts of the method for providing a trained function and/or one of the aspects thereof when the program sections are executed by the training unit.

The present embodiments may further relate to a computer program or computer-readable storage medium including a trained function provided by a proposed computer-implemented method or one of the aspects thereof.

An extensively software-based implementation has the advantage that it is also possible to retrofit providing units and/or training units used to date in a simple way by a software update in order to work in the manner according to the present embodiments. In addition to the computer program, such a computer program product may optionally include additional parts such as, for example, documentation and/or additional components, and also hardware components, such as, for example, hardware keys (e.g., dongles, etc.) for using the software.

BRIEF DESCRIPTION OF THE DRAWINGS

Exemplary embodiments are depicted in the drawings and will be described in more detail below. In different figures, the same reference characters denote the same features.

DETAILED DESCRIPTION

Figure 1:
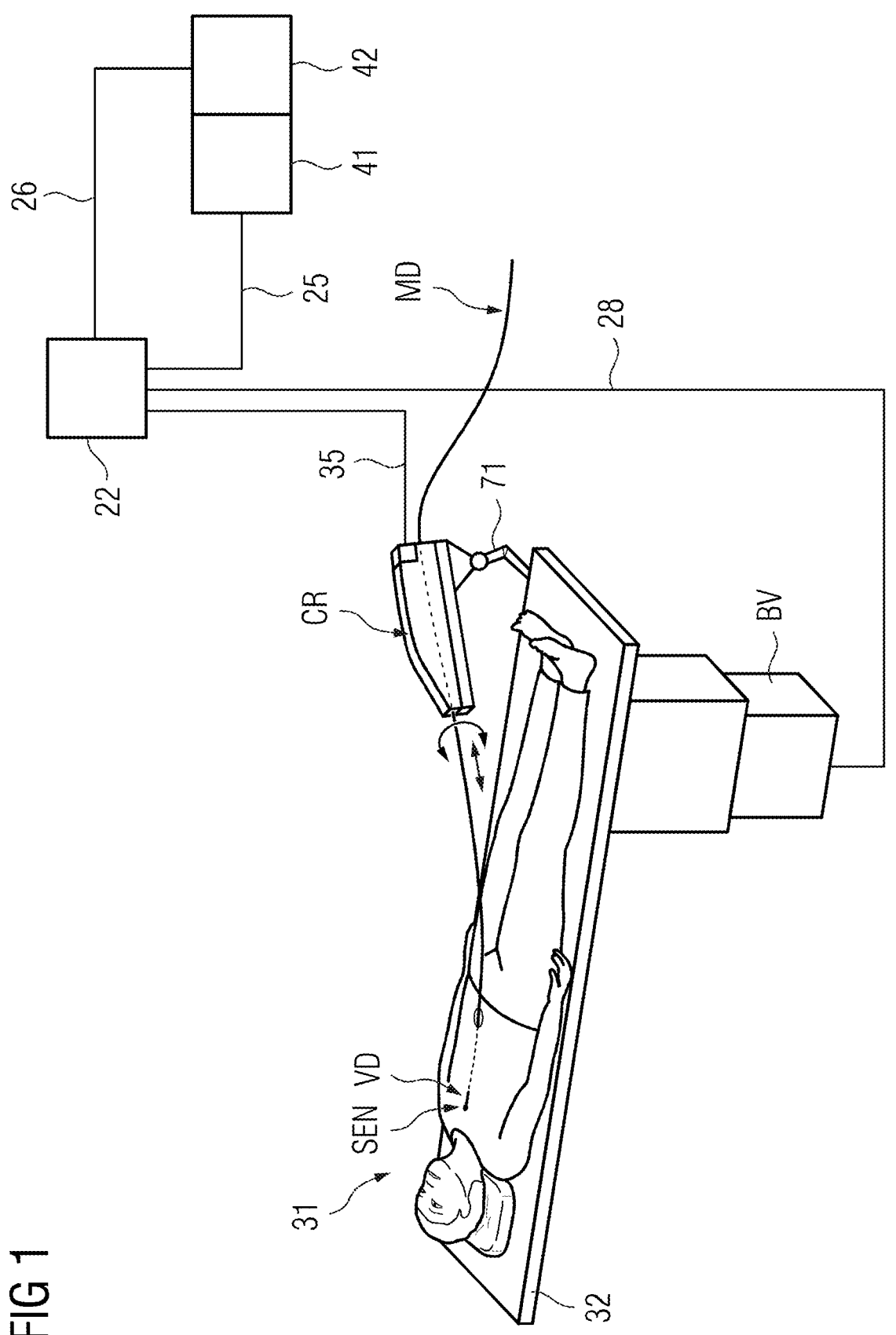
FIGS. 1 and 2 show schematic depictions of different embodiments of a proposed apparatus for positioning a medical object and a proposed system.

FIG. 1 shows a schematic depiction of a proposed apparatus for positioning a medical object and a proposed system. Herein, the apparatus may include a moving apparatus CR for robotically moving the medical object MD. The moving apparatus CR may, for example, be embodied as a catheter robot (e.g., for the remote manipulation of the medical object MD). The medical object MD may be embodied as, for example, an elongated, surgical instrument and/or a diagnostic instrument. For example, the medical object MD may be flexible and/or mechanically deformable. The medical object MD may, for example, be embodied as a catheter and/or endoscope and/or guide wire. In one embodiment, the medical object MD may be introduced into an examination object 31 (e.g., into a hollow organ of the examination object 31) arranged on the patient support apparatus 32 via an introducer sheath. Herein, the patient support apparatus 32 may be at least partially movable. For this purpose, the patient support apparatus 32 may include, for example, a moving apparatus BV. The moving apparatus BV is controllable by a signal 28 from the providing unit 22.

Further, the medical object MD may include a predefined section VD. Herein, the predefined section VD may, for example, describe a tip and/or a section including a marker structure on the medical object MD. The predefined section VD of the medical object MD may at least partially be arranged in the examination object (e.g., the hollow organ). Herein, the hollow organ may, for example, include a vascular section in which the predefined section VD is at least partially arranged.

Further, the moving apparatus CR may be fastened (e.g., such that the moving apparatus CR may move) using a fastening element 71 (e.g., a stand and/or robot arm) on the patient support apparatus 32. In one embodiment, the moving apparatus CR may be embodied to move the medical object MD arranged therein in a translational manner at least along a longitudinal extension direction of the medical object MD. Further, the moving apparatus CR may be embodied to rotate the medical object MD about the longitudinal extension direction. Alternatively or additionally, the moving apparatus CR may be embodied to control a movement of at least part of the medical object MD (e.g., a distal section and/or a tip of the medical object MD). Further, the moving apparatus CR may be embodied to deform the predefined section VD of the medical object MD in a defined manner (e.g., via a cable pull within the medical object MD).

The apparatus may further include a providing unit 22. Herein, the apparatus (e.g., the providing unit 22) may be embodied to receive a control specification. The reception of the control specification may, for example, include capturing and/or reading a computer-readable data memory and/or reception from a data memory unit (e.g., a database). Further, the control specification may be provided by an input unit 42 for capturing input from an operator. The input unit 42 may, for example, include a keyboard and/or a pointing device (e.g., a computer mouse). Further, the apparatus may include a depicting unit 41 (e.g., a monitor and/or a display). Herein, the input unit 42 may be at least partially integrated in the depicting unit 41 (e.g., in the case of a capacitive and/or resistive input display).

The control specification may include at least one command for control (e.g., step-by-step control) of the moving apparatus CR. For example, the control specification may include at least one command (e.g., a temporal sequence of commands) for specifying a translation and/or rotation (e.g., simultaneous translation and rotation) of the medical object MD (e.g., the predefined section VD) by the moving apparatus CR. In one embodiment, the providing unit 22 may be embodied to translate the control specification and to control the moving apparatus CR based thereon. Moreover, the moving apparatus CR may be embodied to position the medical object MD based on the control specification (e.g., to move the medical object MD in a translational and/or rotational manner).

The apparatus (e.g., the providing unit 22) may further be embodied to receive positioning information on the predefined section VD. The positioning information may include information on a spatial position and/or alignment and/or pose (e.g., instantaneous) of the predefined section VD in the examination object 31.

In one embodiment, the control specification may include a specification for spatial positioning (e.g., a length dimension along the longitudinal extension direction of the medical object MD and/or an angle of the medical object MD, and/or a relative movement of the medical object MD, such as the predefined section VD) with respect to the moving apparatus CR. The positioning information may also include information on the spatial positioning of the predefined section VD (e.g., the length dimension along the longitudinal extension direction of the medical object MD and/or the angle of the medical object MD) with respect to the moving apparatus CR.

Herein, FIG. 1 shows an embodiment of the proposed system, including a proposed apparatus and a capturing unit SEN, where the capturing unit is embodied to capture the positioning and/or change in positioning of the predefined section VD in the examination object 31. Further, the capturing unit SEN may be embodied to determine the positioning information based on the captured positioning and/or change in positioning and provide it to the apparatus (e.g., the providing unit 22), for example, by a signal 35. The capturing unit SEN may include a sensor (e.g., an electromagnetic and/or optical and/or acoustic, such as ultrasound-based, and/or gyroscopic sensor) embodied to detect the predefined section VD. The capturing unit SEN may, for example, be arranged in and/or on the medical object MD (e.g., the predefined section VD). For example, the capturing unit SEN may at least partially be arranged integrated in the medical object MD (e.g., the predefined section VD).

Alternatively or additionally, the apparatus may be embodied to determine the positioning information by applying a trained function to the control specification, where at least one parameter of the trained function (TF) is based on a comparison of training positioning information (TPI) with comparison positioning information (VPI).

The apparatus (e.g., the providing unit 22) may further be embodied to determine a degree of deviation, where the degree of deviation describes a deviation between the control specification and the positioning information. Further, the apparatus (e.g., the providing unit 22) may be embodied to determine a correction specification for minimizing the deviation based on the degree of deviation. The moving apparatus CR may further be embodied to reposition the predefined section VD based on the correction specification.

Herein, the input of the operator at the input unit 42 may enable a control (e.g., supplementary control) of the apparatus (e.g., the moving apparatus CR), and/or the system, and/or the patient support apparatus 32. For this purpose, the input element 42 may, for example, send a signal 26 to the providing unit 22.

Further, the depicting unit 41 may be embodied to display information and/or graphical depictions of information from the apparatus (e.g., the moving apparatus CR), and/or the system (e.g., the control specification), and/or the positioning information, and/or the degree of deviation, and/or the correction specification. For this purpose, the providing unit 22 may, for example, send a signal 25 to the depicting unit 41.

Figure 2:
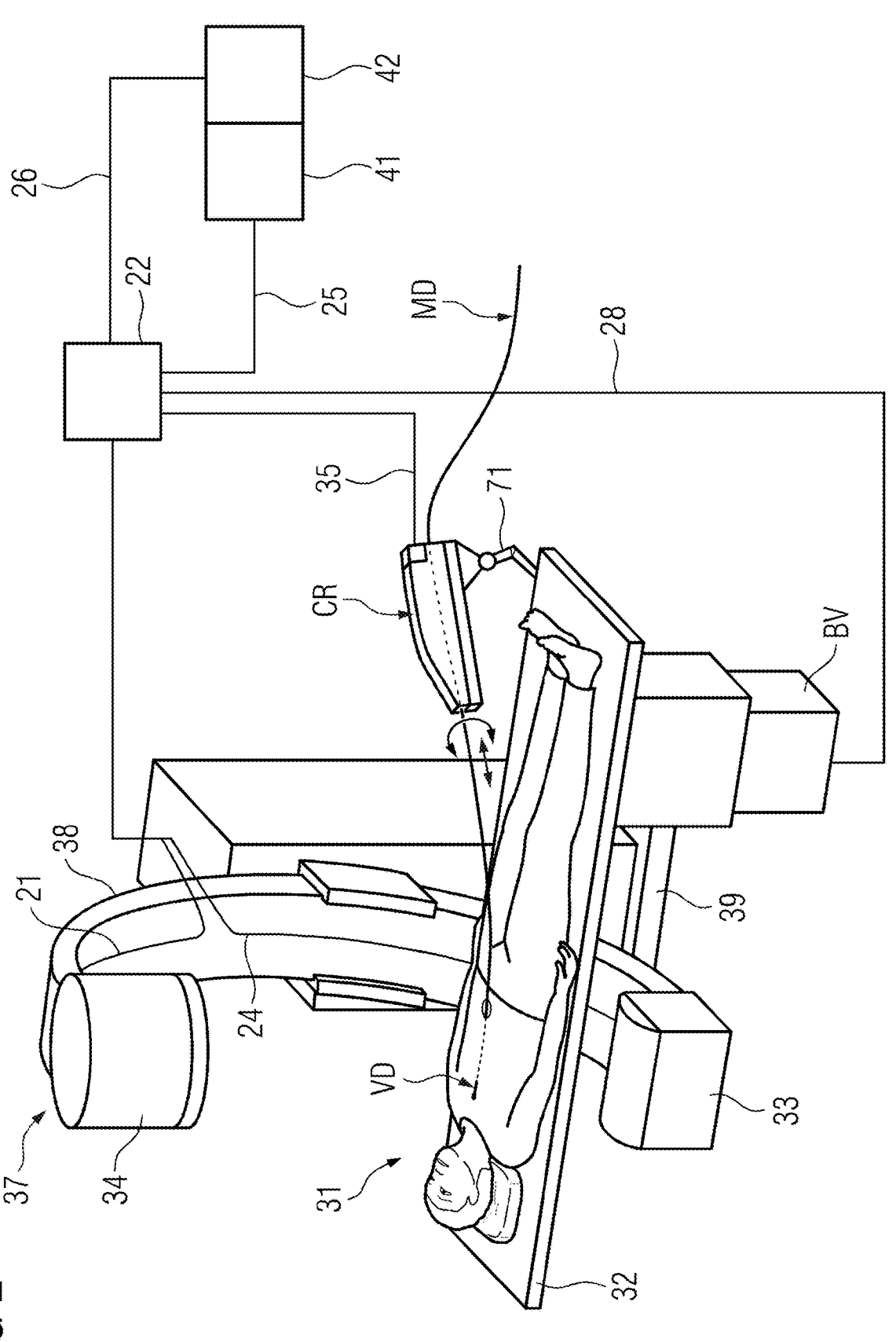

FIG. 2 shows a further embodiment of the proposed system, where the capturing unit SEN may include a medical imaging device (e.g., a medical C-arm X-ray device 37). The medical C-arm X-ray device 37 may be embodied to record medical image data from the examination object 31.

In the exemplary embodiment, as a medical C-arm X-ray device 37, the medical imaging device may include a detector 34 (e.g., an X-ray detector) and an X-ray source 33. To record the image data, the arm 38 of the medical C-arm X-ray device 37 may be mounted such that the arm 38 may move about one or more axes. Further, the medical C-arm X-ray device 37 may include a moving apparatus 39 that enables the medical C-arm X-ray device 37 to move in space. The detector 34 and the X-ray source 34 may be fastened such that the detector 34 and the X-ray source 34 may move in a defined arrangement on a common C-arm 38.

The providing unit 22 may also be embodied to control a positioning of the medical C-arm X-ray device 37 relative to the examination object 31 such that the predefined section VD of the medical object MD is mapped in the medical image data recorded by the medical C-arm X-ray device 37. The positioning of the medical C-arm X-ray device 37 relative to the examination object 31 may, for example, include positioning the defined arrangement of X-ray source 33 and detector 34 (e.g., the C-arm 38, about one or more spatial axes). Further, the medical C-arm X-ray device 37 may include a moving apparatus 39 (e.g., a wheel system and/or rail system and/or robot arm) that enables movement of the medical C-arm X-ray device 37 in space.

To record the medical image data from the examination object 31, the providing unit 22 may send a signal 24 to the X-ray source 33. In response, the X-ray source 33 may emit an X-ray beam (e.g., a cone beam and/or fan beam and/or parallel beam). When, after interaction with the examination area of the examination object 31 to be mapped, the X-ray beam impinges on a surface of the detector 34, the detector 34 may send a signal 21 to the providing unit 22. The providing unit 22 may, for example, receive the medical image data based on the signal 21.

In one embodiment, the predefined section VD may be mapped in a time-resolved manner in the medical image data. Herein, the capturing unit SEN (e.g., the medical C-arm X-ray device 37) may be embodied to capture the positioning and/or change in positioning of the predefined section VD based on the medical image data. The depicting unit 41 may further be embodied to display a graphical depiction of the medical image data.

Figure 3:
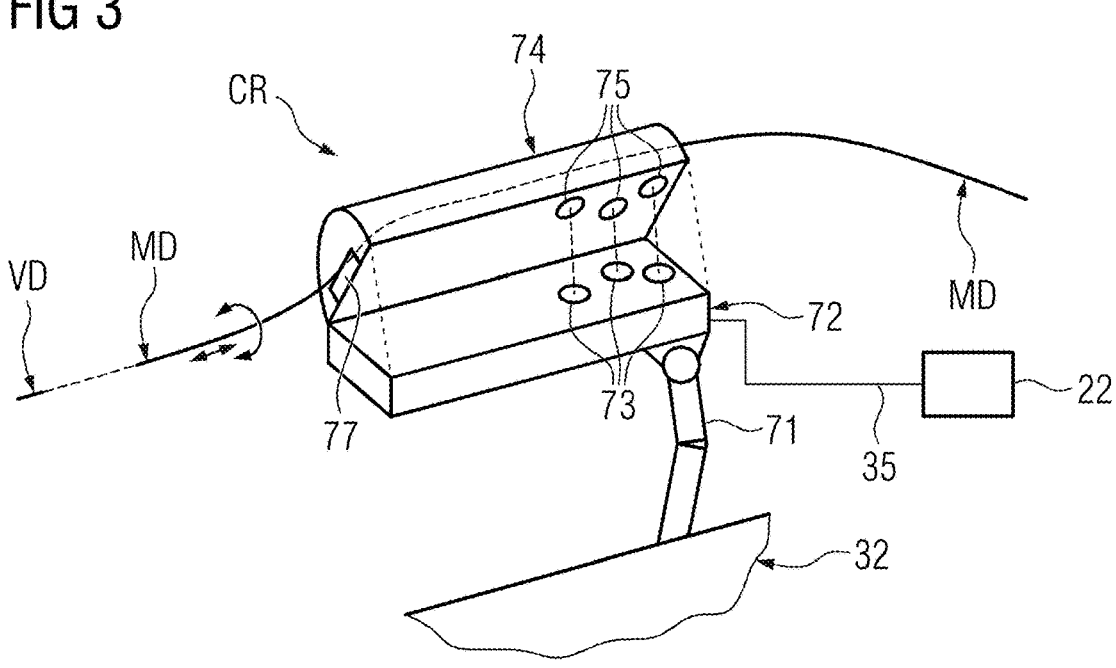
FIG. 3 shows a schematic depiction of a moving apparatus.

FIG. 3 shows a schematic depiction of the moving apparatus CR for robotically moving the medical object MD. In one embodiment, the moving apparatus CR may include a fastening element 71 (e.g., a movable and/or mobile fastening element 71). Further, the moving apparatus CR may include a cassette element 74 embodied to record at least part of the medical object MD. Further, the moving apparatus CR may include a moving element 72 fastened to the fastening element 71 (e.g., a stand and/or robot arm). The fastening element 71 may also be embodied to fasten the moving element 72 to the patient support apparatus 32 (e.g., such that the fastening element 71 may move). Further, the moving element 72 may include at least one (e.g., three) actuator elements 73 (e.g., an electric motor), where the providing unit 22 is embodied to control the at least one actuator element 73. In one embodiment, the cassette element 74 may be coupled (e.g., mechanically and/or electromagnetically and/or pneumatically) to the moving element 72 (e.g., the at least one actuator element 73). Herein, the cassette element 74 may further include at least one transferring element 75 that may be moved by the coupling between the cassette element 74 and the moving element 72 (e.g., the at least one actuator element 73). For example, the at least one transferring element 75 may be motion-coupled to the at least one actuator element 73. Further, the transferring element 75 may be embodied to transfer a movement of the actuator element 73 to the medical object MD such that the medical object MD is moved along a longitudinal extension direction of the medical object MD and/or the medical object MD is rotated about the longitudinal extension direction. The at least one transferring element 75 may, for example, include a roll and/or roller and/or diaphragm and/or shear plate.

In one embodiment, the moving element 72 may include a plurality of actuator elements 73 (e.g., independently controllable actuator elements). Further, the cassette element 74 may include a plurality of transferring elements 75 (e.g., at least one motion-coupled transferring element 75 for each of the actuator elements 73). This enables a movement (e.g., an independent and/or simultaneous movement) of the medical object MD along different degrees of freedom of movement.

Further, the moving apparatus CR (e.g., the at least one actuator element 73) may be controlled by the signal 35 from the providing unit 22. This enables the movement of the medical object MD to be controlled (e.g., indirectly) by the providing unit 22. The alignment and/or position of the moving apparatus CR relative to the examination object 31 may also be adjusted by a movement of the fastening element 71. The moving apparatus CR may be embodied to receive the control specification.

Further, the moving apparatus CR may include a sensor unit 77 embodied to capture a relative movement of the medical object MD relative to the moving apparatus CR. Herein, the sensor unit 77 may, for example, include an encoder (e.g., a wheel encoder and/or a roller encoder), and/or an optical sensor (e.g., a barcode scanner and/or a laser scanner and/or a camera), and/or an electromagnetic sensor. For example, the sensor unit 77 may be at least partially arranged integrated in the moving element 72 (e.g., the at least one actuator element 73) and/or the cassette element 74 (e.g., the at least one transferring element 75). The sensor unit 77 may, for example, be embodied to capture the relative movement of the medical object MD by capturing the medical object MD relative to the moving apparatus CR. Alternatively or additionally, the sensor unit 77 may be embodied to capture a movement and/or change in position of components of the moving apparatus CR that are motion-coupled to the medical object MD (e.g., the at least one actuator element 73 and/or the at least one transferring element 74).

Figure 4:
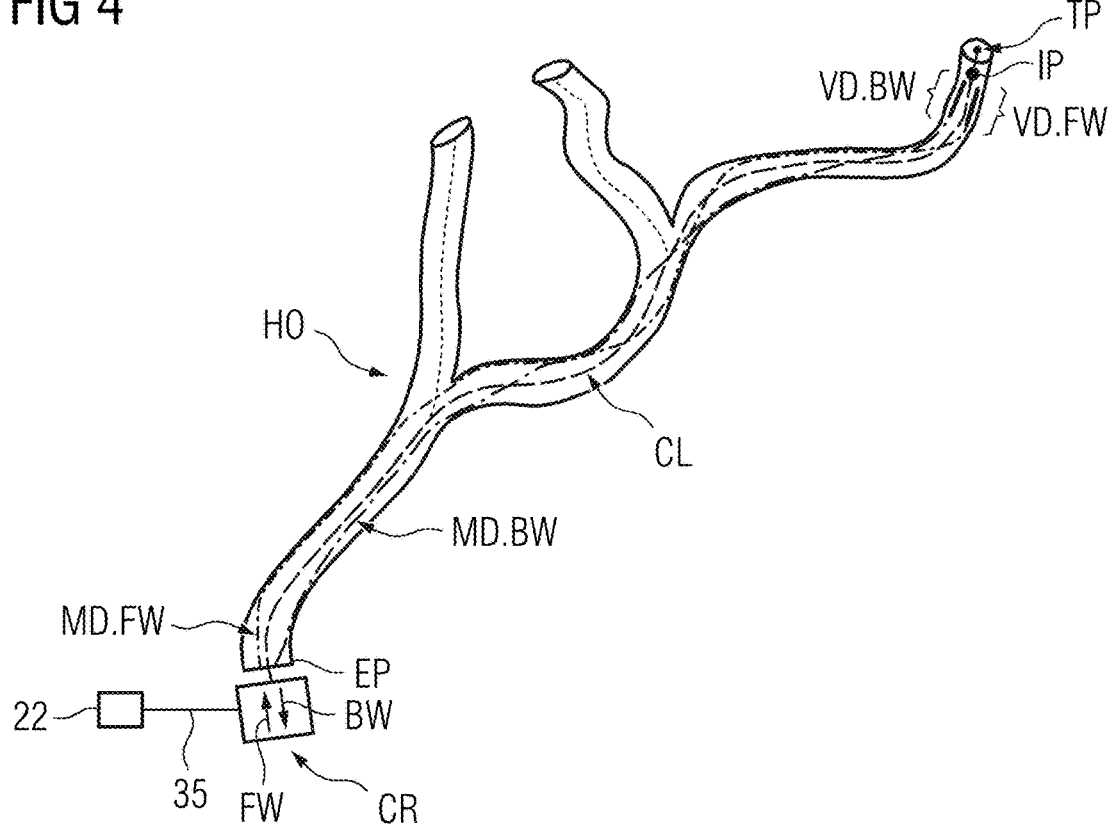
FIG. 4 shows a schematic depiction of the positioning of the predefined section.

FIG. 4 shows a schematic depiction of the positioning of the predefined section VD in a hollow organ HO (e.g., a vascular section) of the examination object 31. The hollow organ HO may, for example, include a vascular section in which the predefined section VD is arranged. In one embodiment, the apparatus may be embodied to determine the degree of deviation in dependence on a direction of movement FW, BW, along which the moving apparatus CR is embodied to position the predefined section VD. In one embodiment, the apparatus (e.g., the providing unit 22) may be embodied to receive a data set including a map and/or a model (e.g., a centerline model) of the examination object (e.g., the hollow organ HO). Herein, the data set may map the examination object 31 (e.g., preoperatively and/or intraoperatively). The apparatus may further be embodied to determine the degree of deviation additionally based on the data set (e.g., with respect to the centerline model).

The centerline model may include at least one centerline CL. The centerline CL describes the spatial course of the hollow organ HO (e.g., at least a vascular section of the examination object 31) spatially (e.g., two-dimensionally and/or three-dimensionally). If the data set (e.g., the centerline model) describes (e.g., maps) the spatial course of the hollow organ HO two-dimensionally, the apparatus may, for example, be embodied to ascertain and supplement depth information by applying an algorithm for estimating the depth information to the data set. Herein, the at least one centerline CL may be a midline of the hollow organ HO, which, in each case, extends along a longitudinal extension direction of the hollow organ HO through the midpoint of the cross-sectional area of the hollow organ HO. For example, the apparatus may be embodied to determine (e.g., to simulate) the initial positioning IP of the predefined section VD and/or the spatial course of the medical object MD based on the control specification in the centerline model.

Herein, a spatial course of the at least one centerline CL from an entry point EP of the medical object MD into the examination object 31 to the spatial target positioning TP of the predefined section VD may describe a mean distance of the medical object MD (e.g., if the medical object MD were to be arranged along the at least one centerline CL). When positioning the predefined section VD along a direction (e.g., a translational direction) of movement FW facing away from the moving apparatus CR, meandering and/or spiraling of the medical object MD.FW in the hollow organ HO may result in a lengthening of the distance from the entry point EP to the target positioning TP compared to the mean distance. Here, the predefined section VD.FW may include the initial positioning IP. Further, when the predefined section VD is positioned along a direction (e.g., translational direction) of movement BW facing the moving apparatus CR, there may be a shortening (e.g., truncation) of the distance from the entry point EP to the target positioning TP compared to the mean distance. In one embodiment, the apparatus may be embodied to determine the deviation (e.g., the degree of deviation) with respect to the centerline model (e.g., the mean distance). Herein, the apparatus may further be embodied to determine the shortening and/or lengthening of the distance from the entry point EP to the target positioning TP compared to the mean distance by determining (e.g., section-by-section) a spatial deviation between the spatial course of the medical object MD.FW, MF.BW and the centerline model (e.g., substantially perpendicular to the at least one centerline CL). Herein, the spatial deviation between the spatial course of the medical object MD.FW, MD.BW and the centerline model may be limited by the spatial extent of the hollow organ HO (e.g., a diameter and/or a cross-sectional area). The apparatus may, for example, be embodied to ascertain the degree of deviation based on the control specification and the centerline model (e.g., in dependence on the direction of movement FW, BW for positioning the predefined section VD). For example, the apparatus may be embodied to ascertain (e.g., to simulate) a relationship between the lengthened MD.FW and the shortened spatial course of the medical object MD.BW (e.g., a difference in length and/or difference in angle) in the examination object 31 based on the control specification and the centerline model.

Further, the apparatus may be embodied to determine (e.g., to verify) the centerline model (e.g., the at least one centerline CL) based on a comparison and/or an averaging of the lengthened MD.FW and the shortened spatial course of the medical object MD.BW in the examination object additionally based on the positioning information. Similarly, the apparatus may be embodied to verify the relationship between the lengthened MD.FW and the shortened spatial course of the medical object MD.BW (e.g., the difference in length and/or difference in angle) in the examination object 31 additionally based on the positioning information. This enables a quality of the determination of the degree of deviation to be improved.

The moving apparatus CR may further be embodied to move the medical object MD for positioning the predefined section VD in an initial positioning IP of the predefined section VD along a first direction of movement FW based on the control specification. Further, the moving apparatus CR may be embodied to move the medical object MD based on a further control specification against BW the first direction of movement such that the predefined section VD.BW starts to leave its initial positioning IP. Herein, the apparatus may be embodied to additionally determine the degree of deviation based on a comparison of the control specification with the further control specification.

Further, the apparatus may be embodied to determine the degree of deviation and the correction specification for different initial positionings IP of the predefined section in the examination object 31 (e.g., in the hollow organ HO). Moreover, the apparatus may be embodied to determine the correction specification for at least one further positioning of the predefined section VD (e.g., the target positioning TP) in the examination object by interpolation and/or extrapolation of the correction specifications determined so far.

Figure 5:
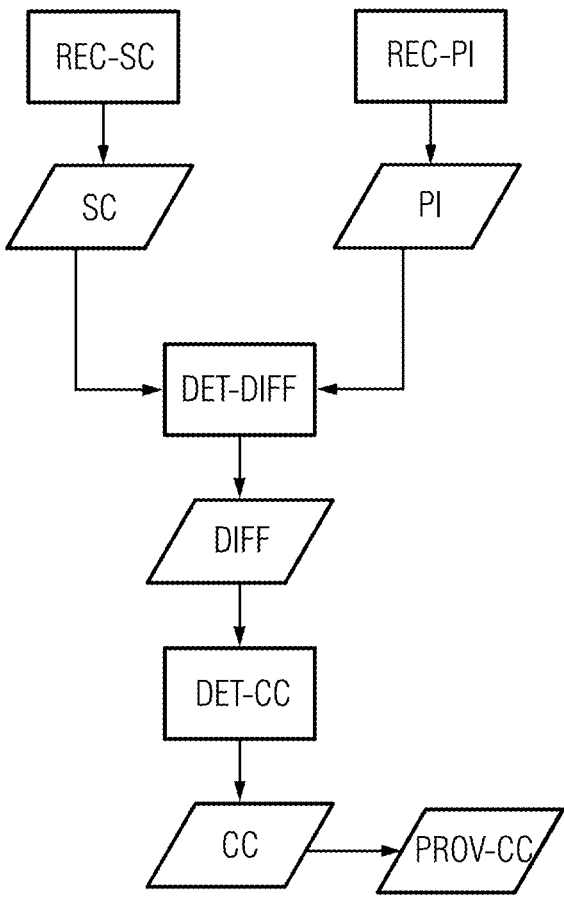
FIGS. 5 to 10 show schematic depictions of different embodiments of a proposed method for providing a correction specification.

FIG. 5 shows a schematic depiction of an embodiment of the method for providing a correction specification PROV-CC. Herein, in a first act a), the control specification SC may be received REC-SC by a proposed apparatus for positioning a medical object MD. Herein, prior to the start of the method, the predefined section VD may have been positioned by the moving apparatus CR based on the control specification SC. In a second act b), the positioning information PI on the predefined section VD of the medical object MD may be received REC-PI. In a third act c), the degree of deviation DIFF may be determined DET-DIFF, where the degree of deviation DIFF describes a deviation between the control specification SC and the positioning information PI. In a fourth act d), the correction specification CC for minimizing the deviation is determined DET-CC based on the degree of deviation DIFF. In a fifth act e), the correction specification CC may be provided PROV-CC.

The control specification SC may, for example, include information on a direction of movement FW, BW, where, prior to the start of the method, the predefined section VD has been positioned along the direction of movement FW, BW by the moving apparatus CR. Further, the degree of deviation CC may be determined DET-CC in act c) in dependence on the direction of movement FW, BW.

Figure 6:
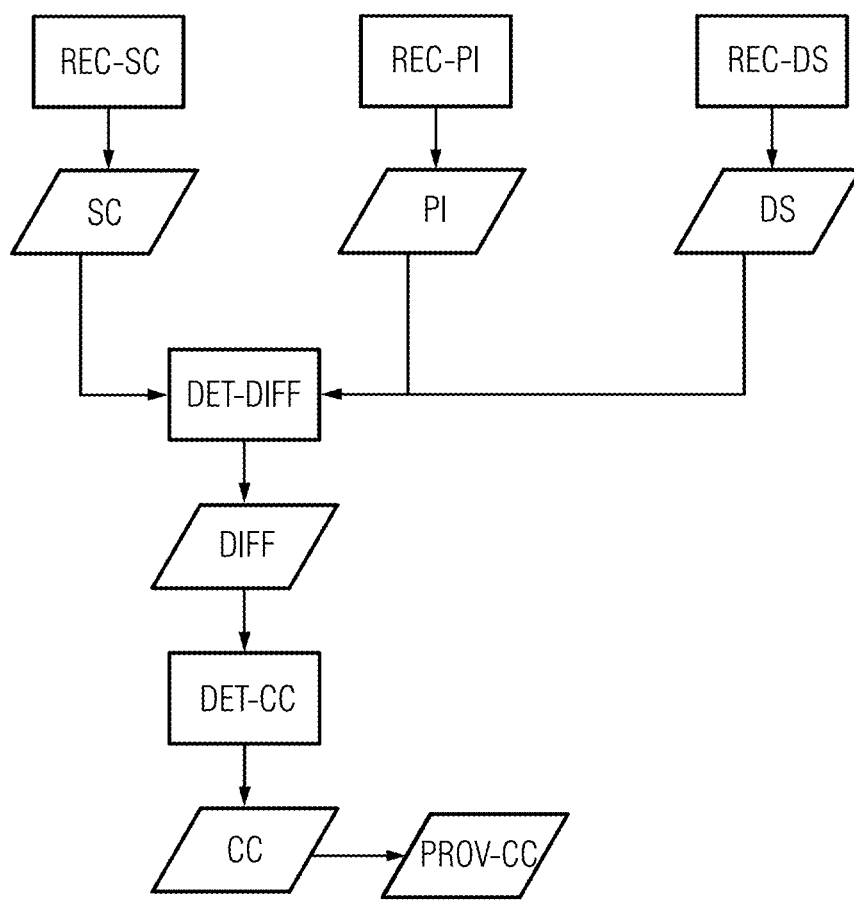

FIG. 6 shows a schematic depiction of a further embodiment of the proposed method for providing a correction specification PROV-CC. Herein, in act a.2), a data set DS including a map and/or a model of the examination object 31 may be received REC-DS. Further, the degree of deviation may, for example, additionally be determined in act c) based on the data set DS and the positioning information PI.

In one embodiment, the data set DS may include a centerline model of a vascular section of the examination object 31, where the predefined section VD is arranged in the vascular section. Further, the degree of deviation DIFF may be determined DET-DIFF in act c) with respect to the centerline model. Herein, the data set DS may map the examination object 31 (e.g., preoperatively and/or intraoperatively).

Figure 7:
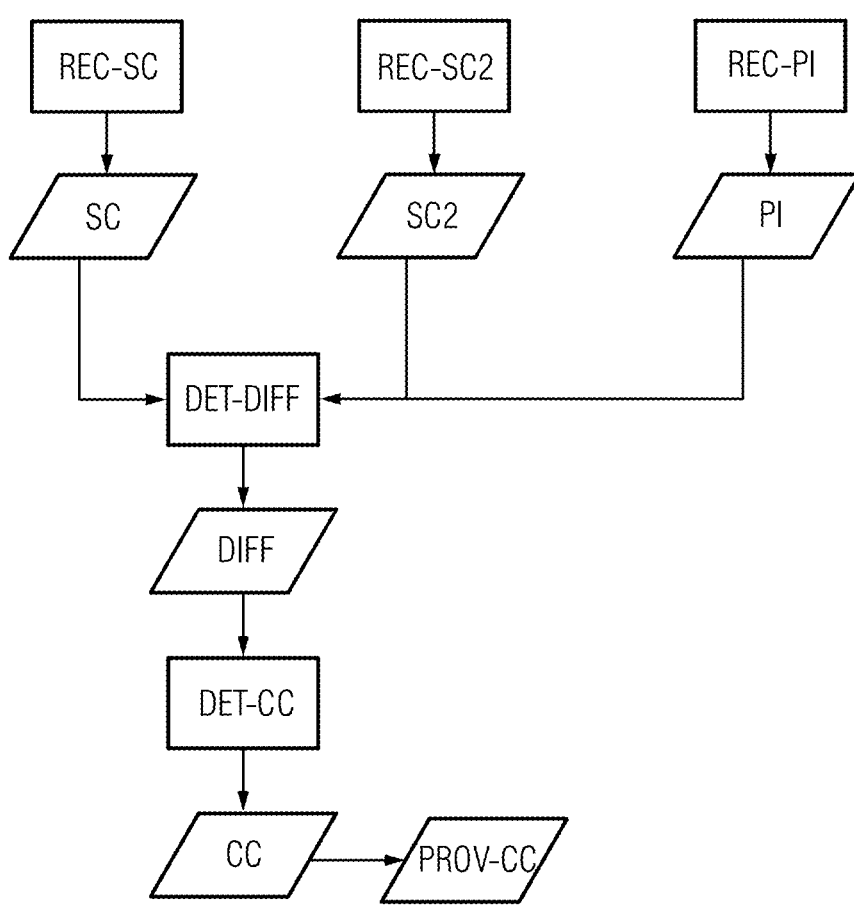

FIG. 7 shows a schematic depiction of a further embodiment of the proposed method for providing a correction specification PROV-CC. Herein, in a further act a.3), a further control specification SC2 may be received by the proposed apparatus. In one embodiment, prior to the start of the method, the medical object MD may have been moved by the moving apparatus CR for positioning the predefined section VD in the initial positioning IP along a first direction of movement FW based on the control specification SC. Further, prior to the start of the method, the medical object MD may have been moved by the moving apparatus CR based on the further control specification SC2 against BW the first direction of movement such that the predefined section VD deviates from an initial positioning IP. Herein, the degree of deviation DIFF may be determined DET-CC in act c) (e.g., based on a comparison COMP-SC-SC2 of the control specification SC with the further control specification SC2).

Figure 8:
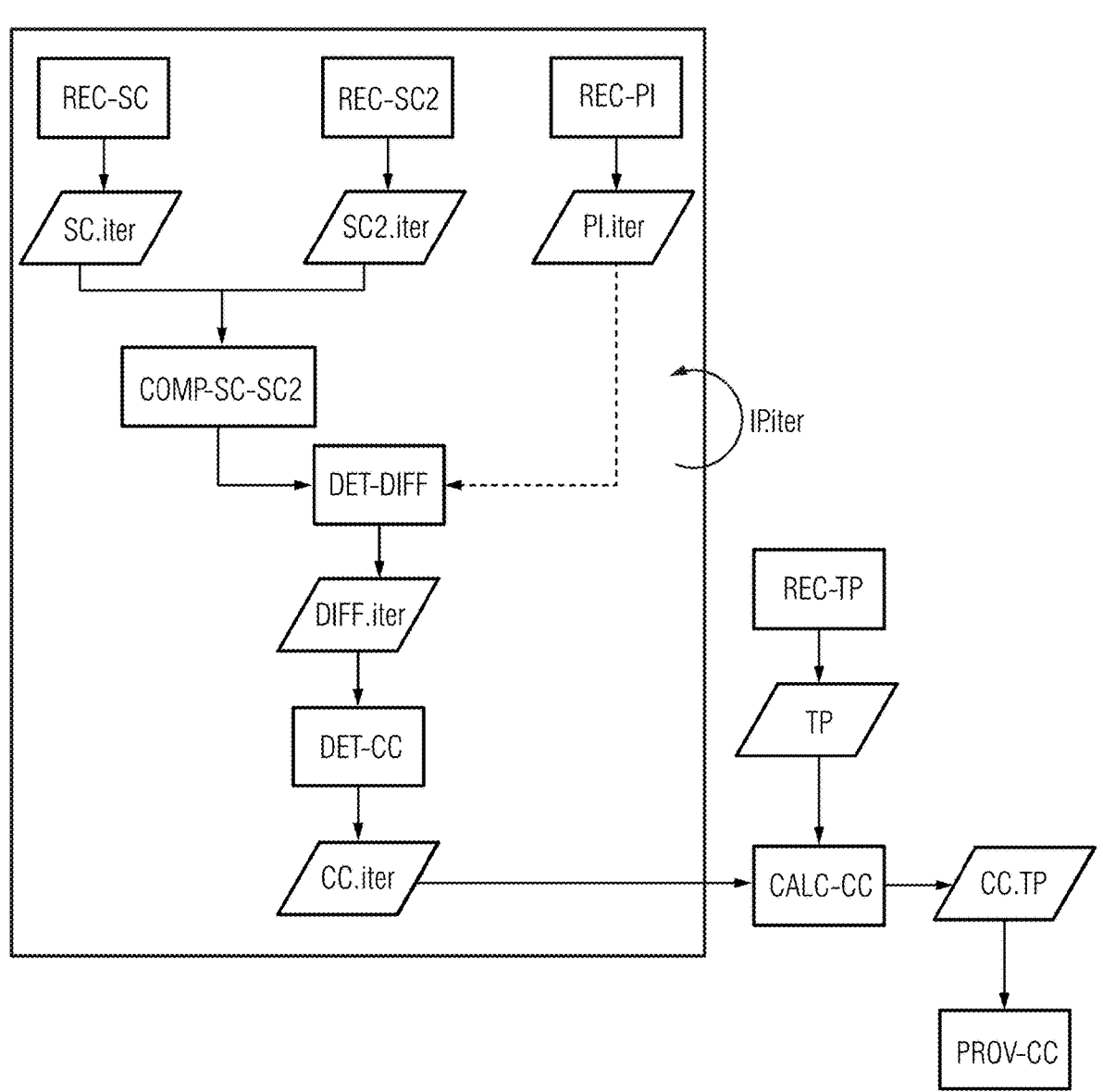

FIG. 8 shows a schematic depiction of a further embodiment of the proposed method for providing a correction specification PROV-CC. Herein, in act a), a plurality of control specifications SC.iter for different initial positionings IP.iter of the predefined section VD in the examination object 31 may be received REC-SC. Further, in act a.3), a plurality of further control specifications SC2.iter for the initial positionings IP.iter of the predefined section VD may be received REC-SC2. In one embodiment, the degree of deviation DIFF.iter and the correction specification CC.iter for the different initial positionings IP.iter in the examination object may be determined DET-DIFF, DET-CC. Thereafter, the correction specification CC-TP for at least one further possible positioning (e.g., the received REC-TP target positioning TP) of the predefined section VD in the examination object may be determined CALC-CC by interpolation and/or extrapolation of the correction specifications CC.ter determined so far.

Figure 9:
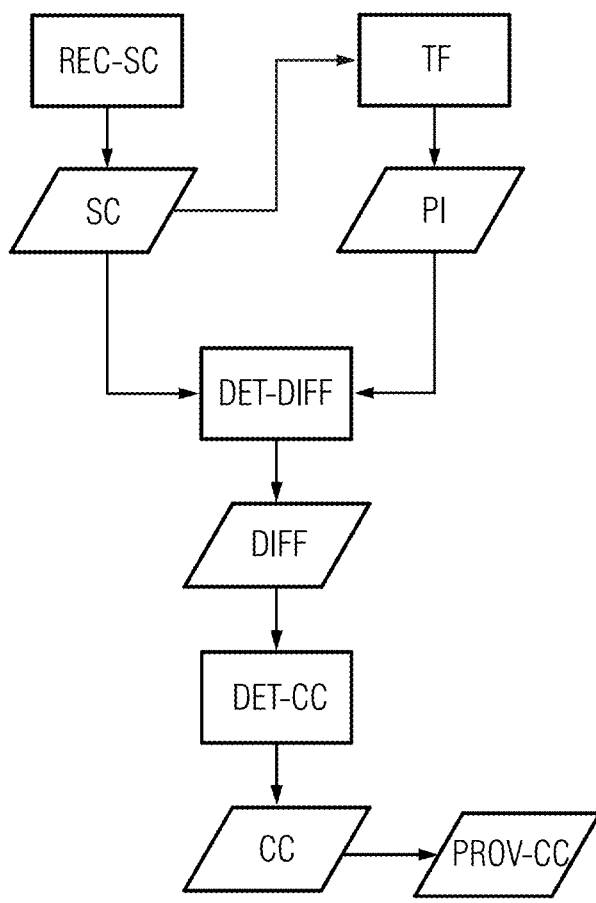

FIG. 9 shows a schematic depiction of a further embodiment of the proposed method for providing a correction specification PROV-CC. Herein, the positioning information PI may be determined in act b) by applying a trained function TF to the control specification SC. In one embodiment, at least one parameter of the trained function TF may be based on a comparison of training positioning information with comparison positioning information.

The movement of the medical object MD may be composed of a translation T and a rotation R. Herein, a distinction may be made between an attack position of the manipulation for moving the medical object MD and an effect position of the resulting positioning of the predefined section VD. If R(CR) describes the rotation and T(CR) describes the translation of the medical object MD at the attack position on the moving apparatus CR, R(VD), and T(VD) may describe the resulting rotation or translation of the predefined section. Hence, the effect of a movement of the medical object MD by the moving apparatus CR on the positioning of the predefined section VD may be described as:

$$[R(VD),T(VD)]=TF[R(CR),T(CR)] \tag{1},$$

where the rotation R(CR) and the translation T(CR) of the medical object MD on the moving apparatus CR are pre-specified by the control specification. Further, the effect of the rotation R(CR) and translation T(CR) of the medical object MD by the moving apparatus CR on the positioning of the predefined section VD may be described by the positioning information. The information contained in the positioning information on the spatial position and alignment (e.g., instantaneous) of the predefined section VD may be described by the translation T (VD) and rotation R (VD) of the predefined section VD. The determination and/or adjustment of the at least one parameter of the trained function TF may, for example, be based on a pair consisting of training input data and associated training output data. Hence, a pair of training data may include training control specifications (e.g., different rotations R (CR) and translations T(CR)) of the medical object MD by the moving apparatus CR, and comparison positioning information on the predefined section (e.g., the rotations R(VD) and translations T(VD) of the predefined section VD corresponding to the rotations R(CR) and translations T(CR) of the medical object). Further, the input data of the trained function TF may also be based on the material parameter and/or the operating parameter of the medical object and/or the physiological parameter of the examination object 31. Further, the input data of the trained function TF may be based on the data set DS (e.g., the centerline model) of the examination object 31 and/or the medical image data ID.

It is also possible to determine the inverse TF⁻¹ of the trained function TF:

$$[R(CR),T(CR)]=TF^{-1}[R(VD),T(VD)] \tag{2}.$$

Figure 10:
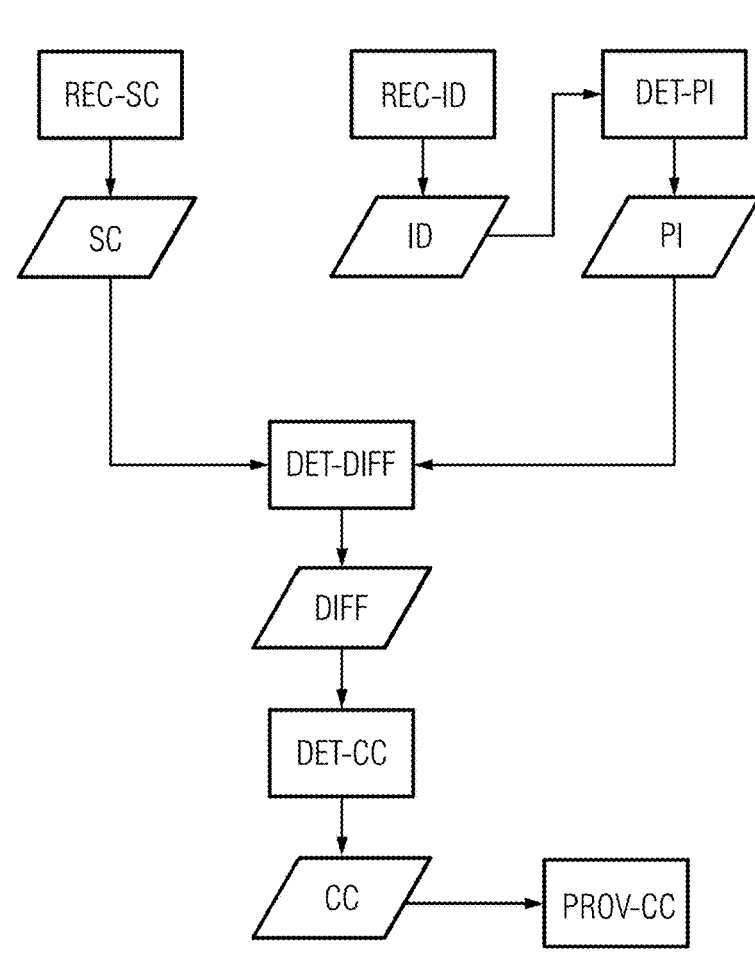

FIG. 10 shows a schematic depiction of a further embodiment of the method for providing a correction specification PROV-CC. Herein, in an act b.0), medical image data ID of the examination object may be received REC-ID by a medical imaging device (e.g., the medical C-arm X-ray device 37). Further, the predefined section VD may be mapped in the medical image data ID in a time-resolved manner. Herein, the positioning information may be determined DET-PI in act b) based on the medical image data ID.

Figure 11:
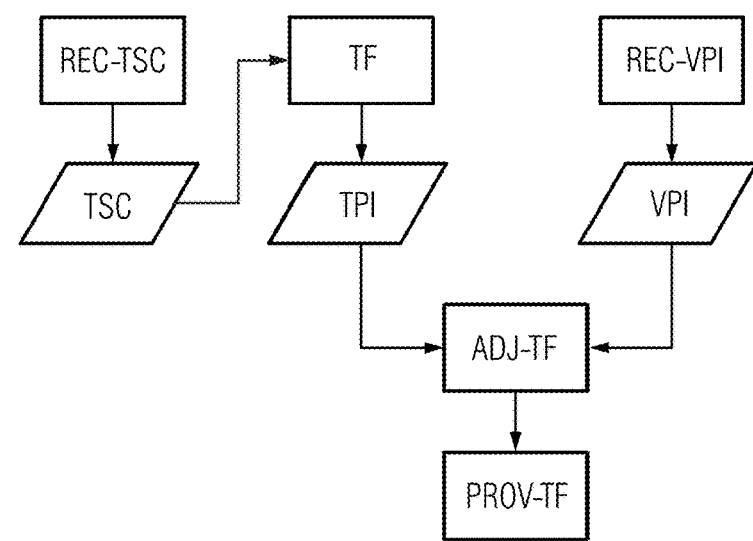
FIG. 11 shows a schematic depiction of a proposed method for providing a trained function.

FIG. 11 shows a schematic depiction of an embodiment of a method for providing a trained function PROV-TF. In a first act t1), training control specifications TSC may be received REC-TSC by a proposed apparatus for positioning a medical object MD. In a second act t2), in each case, comparison positioning information VPI for each of the training control specifications TSC for the predefined section VD of the medical object MD may be received REC-VPI. In a third act t3), training positioning information TPI may be determined by applying the trained function TF to the training control specifications TSC. Further, in act t4), at least one parameter of the trained function TF may be adjusted ADJ-TF based on a comparison of the training positioning information TPI with the comparison positioning information VPI. Thereafter, the trained function TF may be provided PROV-TF in act t5).

Figure 12:
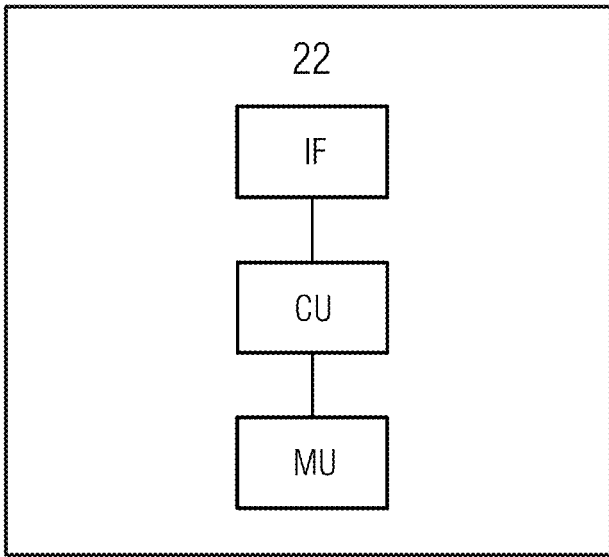
FIG. 12 shows a schematic depiction of a providing unit.

FIG. 12 shows a schematic depiction of a proposed providing unit 22. Herein, the providing unit 22 may include an interface IF, a computing unit CU, and a memory unit MU. The providing unit 22 may be embodied to execute a method for providing a correction specification PROV-CC and the aspects thereof in that the interface IF, the computing unit CU, and the memory unit CU are embodied to execute the corresponding method acts. For example, the interface IF may be embodied to execute acts a) (e.g., the further subacts a.1) to a.3), b), such as the further subact b.0) and/or e). Further, the computing unit CU and/or the memory unit MU may be embodied to execute the other acts.

Figure 13:
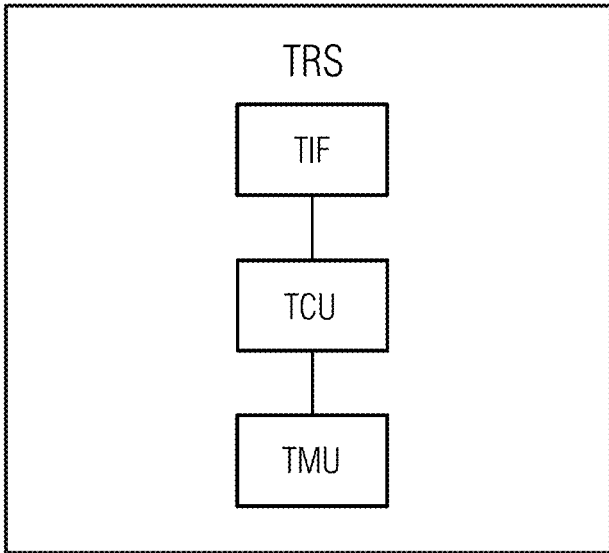
FIG. 13 shows a schematic depiction of a training unit.

FIG. 13 shows a schematic depiction of a proposed training unit TRS. The training unit TRS may include a training interface TIF, a training memory unit TMU, and a training computing unit TCU. The training unit TRS may be embodied to execute a method for providing a trained function PROV-TF and the aspects thereof in that the training interface TIF, the training memory unit TMU, and the training computing unit TCU are embodied to execute the corresponding method acts. For example, the training interface TIF may be embodied to execute acts t1), t2), and/or t5). Further, the training computing unit TCU and/or the training memory unit TMU may be embodied to execute acts t3) and t4).

The providing unit 22 and/or the training unit TRS may, for example, be a computer, a microcontroller, or an integrated circuit. Alternatively, the providing unit 22 and/or the training unit TRS may be a real or virtual group (a technical term for a real group is "cluster"; a technical term for a virtual group is "cloud"). The providing unit 22 and/or the training unit TRS may also be embodied as a virtual system executed on a real computer or a real or virtual group of computers (e.g., virtualization).

An interface IF and/or a training interface TIF may be a hardware or software interface (e.g., PCI bus, USB, or Firewire). A computing unit CU and/or a training computing unit TCU may include hardware elements or software elements (e.g., a microprocessor or a field programmable gate array (FPGA)). A memory unit MU and/or a training memory unit TMU may be implemented as a non-permanent working memory (e.g., random access memory (RAM)) or as a permanent mass memory (e.g., hard disk, USB stick, SD card, solid state disk).

The interface IF and/or the training interface TIF may, for example, include a plurality of sub-interfaces that execute the different acts of the respective method. In other words, the interface IF and/or the training interface TIF may also be understood as a large number of interfaces IF or a large number of training interfaces TIF. The computing unit CU and/or the training computing unit TCU may, for example, include a plurality of sub-computing units that execute the different acts of the respective method. In other words, the computing unit CU and/or the training computing unit TCU may also be understood as a large number of computing units CU or a large number of training computing units TCU.

The schematic depictions contained in the described figures do not represent any kind of scale or size ratio.

Reference is made once again to the fact that the methods described above in detail and the apparatuses depicted are merely exemplary embodiments that may be modified in a wide variety of ways by the person skilled in the art without leaving the scope of the invention. Further, the use of the indefinite article "a" or "an" does not preclude the possibility that the features in question may also be present on a multiple basis. Likewise, the terms "unit" and "element" do not preclude the possibility that the components in question may consist of a plurality of interacting sub-components that may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for positioning a medical object, the apparatus comprising:

a moving apparatus operable to robotically move the medical object, wherein the medical object comprises a predefined section, wherein the predefined section includes a tip of the medical object, a section including a marker structure on the medical object, or the tip of the medical object and the section including the marker structure on the medical object, and is configured to be at least partially arranged in an examination object; and a processor configured to receive a control specification, the control specification including a specification for spatial positioning with respect to the examination object, an angle of the medical object with respect to the examination object, a relative movement of the medical object with respect to the examination object, or any combination thereof, wherein the moving apparatus is configured to position the predefined section based on the control specification, wherein the processor is further configured to:

receive positioning information on the predefined section from a memory, a sensor, or an imaging device, the positioning information including information on an instantaneous spatial position, alignment, pose, or any combination thereof of the predefined section in the examination object;

determine a degree of deviation, wherein the degree of deviation describes a deviation between a target positioning of the predefined section prescribed by the control specification and an actual positioning of the predefined section described by the positioning information; and determine a correction specification for minimizing the deviation based on the degree of deviation, wherein the moving apparatus is further configured to reposition the predefined section based on the correction specification, wherein the processor is further configured to receive a data set comprising a centerline model of a vascular section of the examination object, wherein the processor being configured to determine the degree of deviation comprises the processor being configured to determine the degree of deviation based on the data set, wherein the predefined section is arranged in the vascular section, wherein the processor is further configured to determine the deviation with respect to the centerline model, wherein the centerline model includes at least one centerline, wherein a spatial course of the at least one centerline from an entry point of the medical object into the examination object to the target positioning of the predefined section describes a mean distance of the medical object, wherein the processor is further configured to determine a shortened distance and a lengthened distance between the entry point and the target positioning of the predefined section compared to the mean distance of the medical object, the processor being configured to determine the shortened distance and the lengthened distance between the entry point and the target positioning of the predefined section compared to the mean distance of the medical object comprising the processor being configured to determine a spatial deviation between a spatial course of the medical object and the centerline model, and wherein the processor being configured to determine the degree of deviation comprises the processor being configured to determine a relationship between the lengthened distance and the shortened distance based on the control specification and the centerline model.

2. The apparatus of claim 1, wherein the positioning information includes the information on the instantaneous spatial position of the predefined section with respect to the moving apparatus, information on an angle of the medical object with respect to the moving apparatus, or the information on the instantaneous spatial position of the predefined section with respect to the moving apparatus and the information on the angle of the medical object with respect to the moving apparatus.

3. The apparatus of claim 1, wherein the data set further comprises a map.

4. A system comprising:

an apparatus for positioning a medical object, the apparatus comprising:

a moving apparatus operable to robotically move the medical object, wherein the medical object comprises a predefined section, wherein the predefined section includes a tip of the medical object, a section including a marker structure on the medical object, or the tip of the medical object and the section including the marker structure on the medical object, and is configured to be at least partially arranged in an examination object; and a processor configured to receive a control specification, the control specification including a specification for spatial positioning with respect to the examination object, an angle of the medical object with respect to the examination object, a relative movement of the medical object with respect to the examination object, or any combination thereof, wherein the moving apparatus is configured to position the predefined section based on the control specification, wherein the processor is further configured to receive positioning information on the predefined section from a capturing unit, the positioning information including information on an instantaneous spatial position, alignment, pose, or any combination thereof of the predefined section in the examination object, determine a degree of deviation, the degree of deviation describing a deviation between a target positioning of the predefined section prescribed by the control specification and an actual positioning of the predefined section described by the positioning information, and determine a correction specification for minimizing the deviation based on the degree of deviation, and wherein the moving apparatus is further configured to reposition the predefined section based on the correction specification; and the capturing unit configured to:

capture the positioning, change in positioning, or the positioning and the change in positioning of the predefined section in the examination object; and determine the positioning information based on the captured positioning, change in positioning, or the positioning and the change in positioning and provide the positioning information to the apparatus, wherein the processor is further configured to receive a data set comprising a centerline model of a vascular section of the examination object, wherein the processor being configured to determine the degree of deviation comprises the processor being configured to determine the degree of deviation based on the data set, wherein the predefined section is arranged in the vascular section, wherein the processor is further configured to determine the deviation with respect to the centerline model, wherein the centerline model includes at least one centerline, wherein a spatial course of the at least one centerline from an entry point of the medical object into the examination object to the target positioning of the predefined section describes a mean distance of the medical object, wherein the processor is further configured to determine a shortened distance and a lengthened distance between the entry point and the target positioning of the predefined section compared to the mean distance of the medical object, the processor being configured to determine the shortened distance and the lengthened distance between the entry point and the target positioning of the predefined section compared to the mean distance of the medical object comprising the processor being configured to determine a spatial deviation between a spatial course of the medical object and the centerline model, and wherein the processor being configured to determine the degree of deviation comprises the processor being configured to determine a relationship between the lengthened distance and the shortened distance based on the control specification and the centerline model.

5. The system of claim 4, wherein the capturing unit includes a medical imaging device that is configured to record medical image data of the examination object, wherein the predefined section in the medical image data is mapped in a time-resolved manner, wherein the capturing unit is configured to capture the positioning, change in positioning, or the positioning and the change in positioning of the predefined section based on the medical image data.

6. A method comprising:

receiving, by a processor of an apparatus for positioning a medical object, a control specification, wherein the apparatus comprises a moving apparatus operable for robotically moving the medical object, wherein the medical object comprises a predefined section, wherein the predefined section includes a tip of the medical object, a section including a marker structure on the medical object, or the tip of the medical object and the section including the marker structure on the medical object, and is configured to be at least partially arranged in an examination object, and wherein the predefined section has been positioned by the moving apparatus based on the control specification, the control specification including a specification for spatial positioning with respect to the examination object, an angle of the medical object with respect to the examination object, a relative movement of the medical object with respect to the examination object, or any combination thereof;

receiving, by the processor, positioning information on the predefined section of the medical object from a memory, a sensor, or an imaging device, the positioning information including information on an instantaneous spatial position, alignment, pose, or any combination thereof of the predefined section in the examination object;

receiving, by the processor, a data set comprising a centerline model of a vascular section of the examination object, wherein the predefined section is arranged in the vascular section;

determining, by the processor, a degree of deviation, wherein the degree of deviation describes a deviation between a target positioning of the predefined section prescribed by the control specification and an actual positioning of the predefined section described by the positioning information, wherein determining the degree of deviation comprises determining the degree of deviation based on the data set, with respect to the centerline model;

determining, by the processor, a correction specification for minimizing the deviation based on the degree of deviation; and repositioning, by the moving apparatus, the predefined section based on the correction specification, wherein the centerline model includes at least one centerline, wherein a spatial course of the at least one centerline from an entry point of the medical object into the examination object to the target positioning of the predefined section describes a mean distance of the medical object, wherein the method further comprises determining a shortened distance and a lengthened distance between the entry point and the target positioning of the predefined section compared to the mean distance of the medical object, the determining of the shortened distance and the lengthened distance between the entry point and the target positioning of the predefined section compared to the mean distance of the medical object comprising determining a spatial deviation between a spatial course of the medical object and the centerline model, and wherein determining the degree of deviation comprises determining a relationship between the lengthened distance and the shortened distance based on the control specification and the centerline model.

7. The method of claim 6, wherein the specification for the spatial positioning includes a length dimension along a longitudinal extension direction of the medical object, and wherein the information on the instantaneous spatial position, alignment, pose, or any combination thereof of the predefined section in the examination object includes the length dimension along the longitudinal extension direction of the medical object, an angle of the medical object with respect to the moving apparatus, or a combination thereof.

8. The method of claim 6, wherein the data set further comprises a map.

9. The method of claim 6, further comprising:

receiving, by the imaging device, medical image data from the examination object, wherein the predefined section in the medical image data is mapped in a time-resolved manner, and wherein the positioning information is determined based on the medical image data.

10. The apparatus of claim 1, wherein the processor is further configured to determine an initial positioning of the predefined section, a spatial course of the medical object, or the initial positioning of the predefined section and the spatial course of the medical object based on the control specification in the centerline model.

* * * * *